(12) United States Patent
Hoflack et al.

US010716869B2

(10) Patent No.: US 10,716,869 B2
(45) Date of Patent: Jul. 21, 2020

(54) RADIOLABELED MACROCYCLIC EGFR INHIBITOR

(71) Applicant: Oncodesign SA, Dijon (FR)

(72) Inventors: Jan Marie Cyriel Jozef Hoflack, Westmalle (BE); Cyril Berthet, Dijon (FR); Petra Marcella Françoise Blom, Destelbergen (BE); Johnny Vercouillie, Tours (FR); Caroline Robic, Nogent sur Marne (FR); Sarah Catoen, Livry-Gargan (FR); Gilles Voit, Dijon (FR); Jean-Bernard Deloye, Dijon (FR)

(73) Assignee: Oncodesign SA, Dijon (FR)

( * ) Notice: Subject to any disclaimer, the term of this patent is extended or adjusted under 35 U.S.C. 154(b) by 0 days.

(21) Appl. No.: 16/080,196

(22) PCT Filed: Feb. 28, 2017

(86) PCT No.: PCT/EP2017/054611
§ 371 (c)(1),
(2) Date: Aug. 27, 2018

(87) PCT Pub. No.: WO2017/148925
PCT Pub. Date: Sep. 8, 2017

(65) Prior Publication Data
US 2019/0054197 A1 Feb. 21, 2019

(30) Foreign Application Priority Data
Feb. 29, 2016 (EP) ..................... 16157885

(51) Int. Cl.
*A61K 51/00* (2006.01)
*A61M 36/14* (2006.01)
*A61K 51/04* (2006.01)
*C07D 498/08* (2006.01)
*C07B 59/00* (2006.01)
*A61B 6/03* (2006.01)
*A61P 35/00* (2006.01)

(52) U.S. Cl.
CPC .......... *A61K 51/0459* (2013.01); *A61B 6/037* (2013.01); *C07B 59/002* (2013.01); *C07D 498/08* (2013.01); *A61P 35/00* (2018.01)

(58) Field of Classification Search
CPC ....... A61B 6/037; C07B 59/002; A61P 35/00; A61K 51/0459
USPC ...................................... 424/1.89
See application file for complete search history.

(56) References Cited

U.S. PATENT DOCUMENTS

| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |

FOREIGN PATENT DOCUMENTS

| WO | 2004105765 A1 | 12/2004 |
| WO | 2014118197 A1 | 8/2014 |

OTHER PUBLICATIONS

Bahce et al. Clin Cancer Res. 2012, 19, 183-193.*
Zhang et al. Curr. Top. Med. Chem. 2007, 7, 1817-1828.*
Ferrieri Handbook Radiopharm.: Radiochem. Appl. 2003, 229-282.*
Memon et al., "PET imaging of patients with non-small cell lung cancer employing an EGF receptor targeting drug as tracer", British Journal of Cancer, vol. 105, No. 12, pp. 1850-1855, Nov. 2011.
Slobbe et al., "Development of [18F]afatinib as new TKI-PET tracer for EGFR positive tumors", Nuclear Medicine and Biology, vol. 41, Issue 9, pp. 749-757, Oct. 2014.
Vlaming et al., "PET-CT imaging with [18F]-getitinib to measure Abcb1a/1b (P-gp) and abcg2 (Bcrp1) mediated drug-drug interactions at the murine blood-brain barrier", Nuclear Medicine and Biology, vol. 41,Issue 11, pp. 833-841, Nov. 2015.
Search Report pertaining to European Application No. 16157885.1 dated Aug. 10, 2016.
Search Report and Written Opinion pertaining to International Application No. PCT/EP2017/054611 dated May 10, 2017.

* cited by examiner

*Primary Examiner* — Michael G. Hartley
*Assistant Examiner* — Sean R Donohue
(74) *Attorney, Agent, or Firm* — Dinsmore & Shohl LLP

(57) ABSTRACT

The present invention relates to 18-Fluor radiolabeled macrocyclic quinazoline compounds, which are suitable as positron emission tomography (PET) tracers for imaging epidermal growth factor receptors (EGFR), and their use in in vivo diagnosis, preclinical and clinical tumour imaging, patient stratification on the basis of mutational status of EGFR, and assessing tumour response to therapeutic treatments. The present invention also describes precursor compounds and methods of preparing the radiotracers. The invention is relevant to any cancer that is influenced or driven by deregulated EGFR, such as, but not limited to, non-small cell lung cancer (NSCLC), pancreatic, hepatocellular, oesophageal, gastric, colorectal, prostate, cervical, renal, ovarian, breast cancers, head and neck squamous cell carcinoma, and malignant glioma.

9 Claims, 12 Drawing Sheets

(A)

(B)

(A)

(B)

(A)

(B)

(A)

(B)

(C)

(D)

(E)

(A)

(B)

(C)

(D)

(A)

(B)

(C)

(D)

(A)

Fig. 9 (A) - Continued
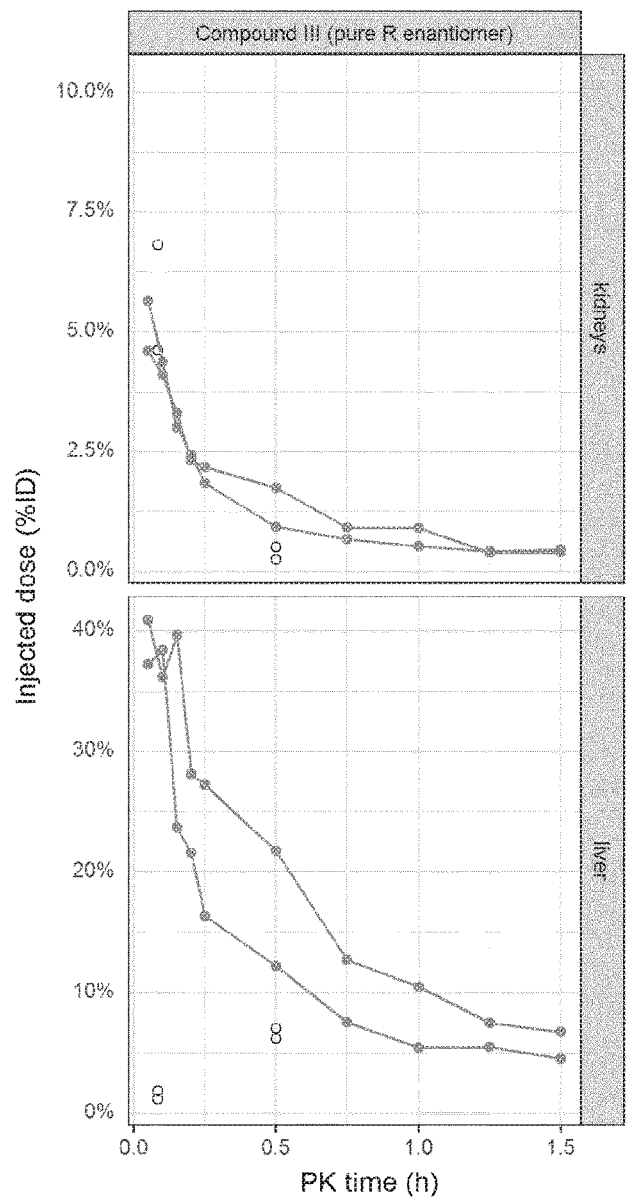

Fig. 9 (B) - Continued
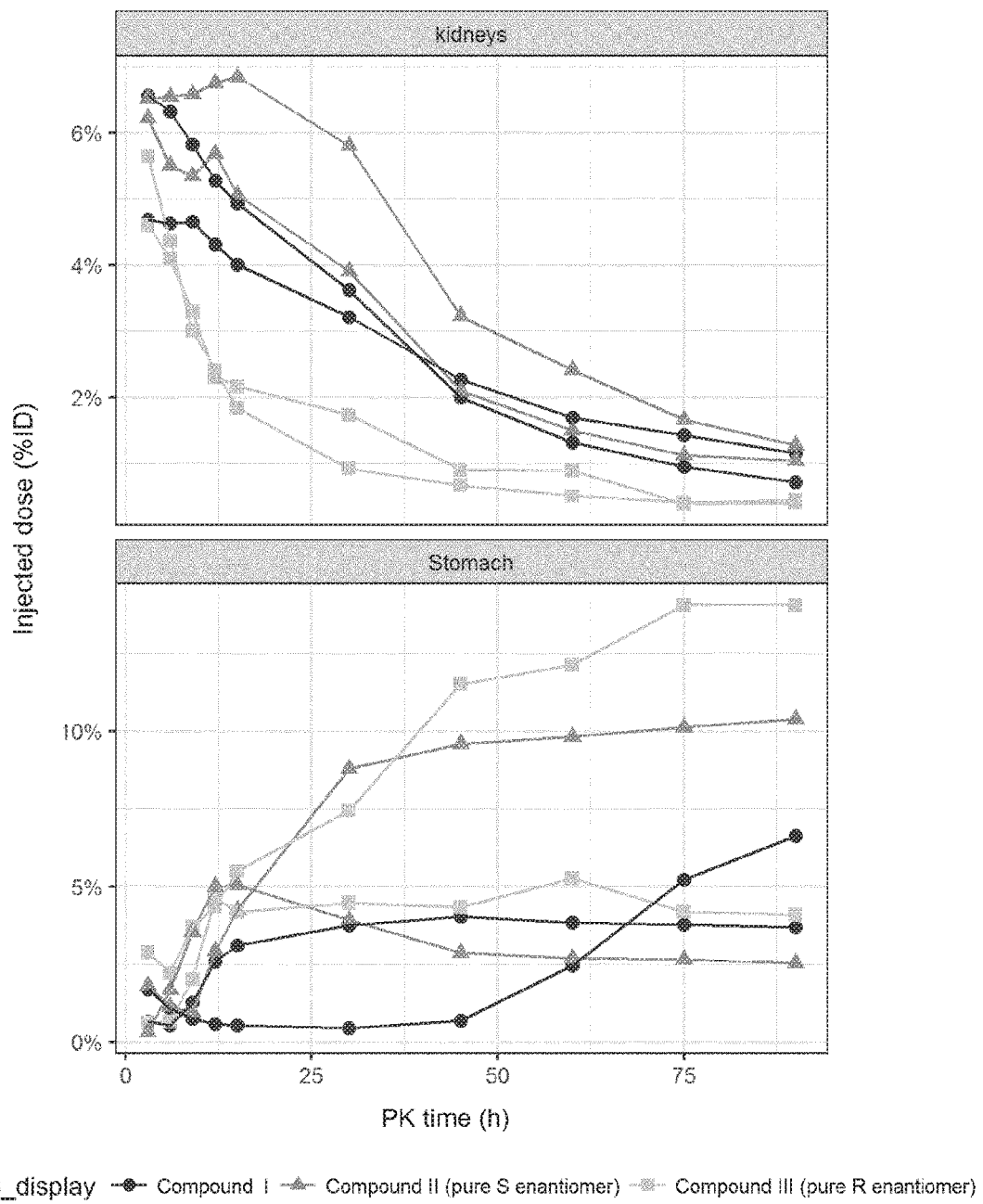

RADIOLABELED MACROCYCLIC EGFR INHIBITOR

FIELD OF THE INVENTION

The present invention relates to 18-Fluor radiolabeled macrocyclic quinazoline compounds, which are suitable as positron emission tomography (PET) tracers for imaging epidermal growth factor receptors (EGFR), and their use in in vivo diagnosis, preclinical and clinical tumour imaging, patient stratification on the basis of mutational status of EGFR, and assessing tumour response to therapeutic treatments. The present invention also describes precursor compounds and methods of preparing the radiotracers. The invention is relevant to any cancer that is influenced or driven by deregulated EGFR, such as, but not limited to, non-small cell lung cancer (NSCLC), pancreatic, hepatocellular, oesophageal, gastric, colorectal, prostate, cervical, renal, ovarian, breast cancers, head and neck squamous cell carcinoma, and malignant glioma.

BACKGROUND TO THE INVENTION

Positron emission tomography (PET) is a nuclear medicine imaging technique that produces images of functional processes of the body. Radiotracers are used in PET as diagnostic tools and to image tissue concentration of molecules of interest.

The development of molecular imaging biomarkers is closely related to the development of therapeutic molecules. Among the potential targets, kinases offer a lot of advantages and notably (i) they play a central role in cellular regulation, (ii) numerous kinase-specific small molecule libraries exist in biotech and pharma industry, (iii) several kinase-targeted therapies are used in clinic (imatinib, sorafenib, sunitinib . . . ) with application across a variety of therapeutic indications. Among the kinases, the epidermal growth factor receptor (EGFR) is an established target for the treatment of advanced non-small cell lung cancer (NSCLC). Three EGFR tyrosine kinase inhibitors (TKIs) gefitinib (Iressa®), erlotinib (Tarceva®) and afatinib (Giotrif®) have already been approved for treatment of NSCLC, and third generation of molecules is under clinical development. Multiple randomized controlled trials have confirmed the association between the presence of activating EGFR mutations (exon 19 del. or L858R point mutation) and objective response to gefitinib, erlotinib and afatinib, thus demonstrating their superiority over platinum-based chemotherapy as first-line treatment for NSCLC patients with EGFR-mutation-positive tumors (10 to 15%) (Sebastian et al., 2014, European Respiratory Review, 23 (131): 92-105). Unfortunately the majority of patients will develop a resistance to the TKI in the long term (6-12 months) despite initially good control. If the mechanism of resistance are not yet fully characterized, most patients (50%) will acquire an additional T790M mutation located in exon 20 of EGFR (Pao et al., 2005, PLoS Medicine, 2(3): e73; Yun et al., 2008, PNAS 105 (6): 2070). Other subgroups of patients will show a resistance due to the amplification of MET protoongene which is responsible for up to 20% of relapsing patients or inactivation of the phosphatase and tensin homolog (PTEN) tumor suppressor gene, leading to the activation of phosphatidylinositol 3-Kinase (PI3K)/AKT pathway (Sequist et al., 2011, Science translational medicine, 3(75): 75ra26). The lack of an established therapeutic option for NSCLC patients who have progressive disease after EGFR-TKIs failure poses a great challenge to physicians in terms of how to best manage this growing group of patients.

PET-imaging with radiolabeled TKIs (TKI-PET) can provide a tool to determine and predict responsiveness to EGFR TKIs in vivo. There is a clinical need for non-invasive technology to early evaluate the treatment responsiveness and determine the spatial and temporal acquisition of molecular mutation leading to tumor resistance. TKI-PET is a potential personalized medicine tool that will guide the physicians to adapt the treatment of their patients, choosing the best treatment or combination of treatments according the spatial and temporal evolution of tumor resistance and its molecular causality.

The present invention provides a new radiolabeled (18-Fluor) compound targeting EGFR evaluated in vitro and in preclinical imaging study. This compound could be useful to predict the activity of EGFR, correlated with its mutational status, and follow-up of this activity in tumors treated by EGFR targeted therapies. Uptake of radiolabeled compound in the tumors can be determined with PET. Examples of this principle with $^{11}$C-erlotinib or $^{18}$F-afatinib are published respectively by Memon et al in British Journal of Cancer, 2011, 1850-1855 and by Slobbe et al in Nuclear Medicine and Biology 41 (2014) 749-757. Macrocyclic quinazoline derivatives have already been described to be suitable antiproliferative agents (WO2004105765), however, we have now surprisingly found that the particular compounds of the invention, are very suitable PET tracers.

The present invention aims to provide radioligands selective for EGFR (erbB1) as PET tracer for in vivo diagnosis, preclinical and clinical tumour imaging, patient stratification on the basis of mutational status of EGFR, and tumour response to therapeutic treatments.

SUMMARY OF THE INVENTION

In a first aspect, the present invention provides a fluorine-18 labeled compound of formula (I), or any prodrug, pharmaceutically acceptable salt, metabolite, polymorph, solvate, hydrate, stereoisomer, radioisotope or tautomer thereof

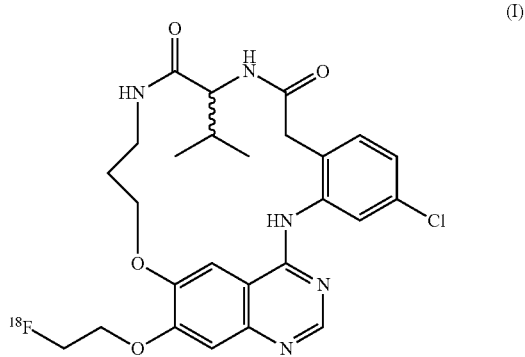 [SMILES: CC(C)C1NC(=O)Cc2ccc(Cl)cc2Nc2ncnc3cc(OCC[18F])c(cc23)OCCCNC1=O]

In a particular embodiment, the present invention provides a fluorine-18 labeled compound according to this invention and having the S-stereoisochemistry as represented in formula (II), or the R-stereoisochemistry as represented in formula (III) or any prodrug, pharmaceutically acceptable salt, metabolite, polymorph, solvate, hydrate, stereoisomer, radioisotope or tautomer thereof; in particular the R-stereoisochemistry as represented in formula (III)

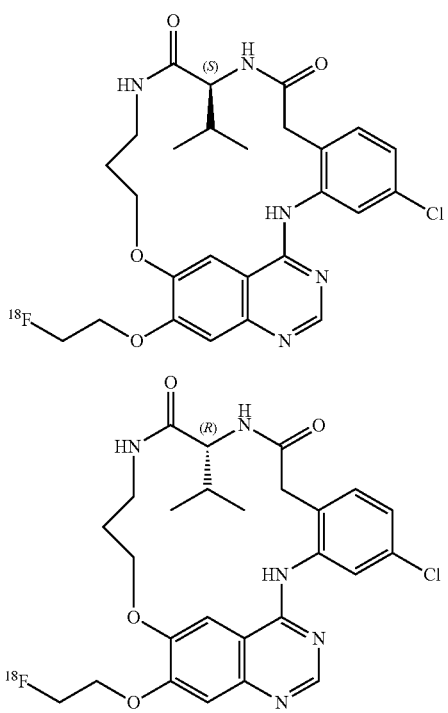

In a further aspect, the present invention provides a radiopharmaceutical composition comprising a radiolabeled compound according to anyone of formula (I), (II) or (III), optionally further comprising one or more inert carriers and/or diluent. In preferred embodiment, the present invention provides a radiopharmaceutical composition comprising a radiolabeled compound according to formula (II), optionally further comprising one or more inert carriers and/or diluent.

In yet a further aspect, the prevent invention provides the use of a radiolabeled compound according to anyone of formula (I), (II) or (III), or a radiopharmaceutical composition comprising a radiolabeled compound according to anyone of formula (I), (II) or (III); as a diagnostic agent in human medicine.

The present invention further provides the use of a radiolabeled compound according to anyone of formula (I), (II) or (III), or a radiopharmaceutical composition comprising a radiolabeled compound according to anyone of formula (I), (II) or (III); in tumor imaging.

In a further aspect, the present invention provides a method for in vivo diagnosis or tumor imaging comprising use of a radiolabeled compound according to anyone of formula (I), (II) or (III), or a radiopharmaceutical composition comprising a radiolabeled compound according to anyone of formula (I), (II) or (III).

In yet a further aspect, the present invention provides a method for diagnostic imaging of an EGFR-associated tumor in a human, which comprises administering to a human in need of such diagnostic imaging an effective amount of a compound according to anyone of formula (I), (II) or (III), or a radiopharmaceutical composition comprising a radiolabeled compound according to anyone of formula (I), (II) or (III); and obtaining an image useful for quantifying EGFR in the tumor of said human using positron emission tomography.

In a further aspect, the present invention provides a method for the quantification of EGFR in human tissue, which comprises contacting such human tissue in which quantification is desired with an effective amount of a compound according to anyone of formula (I), (II) or (III), or a radiopharmaceutical composition comprising a radiolabeled compound according to anyone of formula (I), (II) or (III); and detecting or quantifying EGFR using positron emission tomography.

In another aspect, the present invention provides a method for preparing a radiolabeled compound according to formula (I); said method comprising the step of reacting radiolabeled

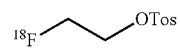

with a compound of formula (Ib)

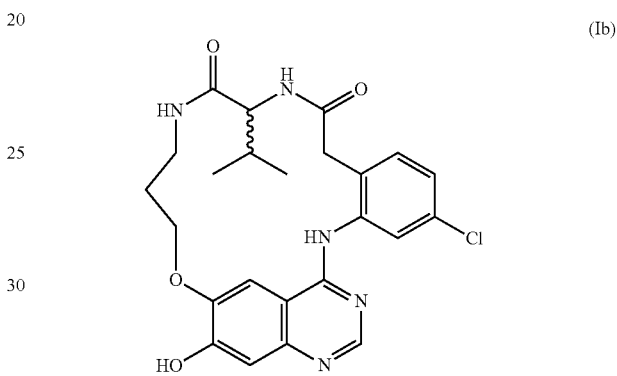

and isolating the resulting compound of formula (I).

In a preferred embodiment, the present invention provides a method for preparing a radiolabeled compound according to formula (III); said method comprising the step of reacting radiolabeled

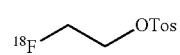

with a compound of formula (IIIb)

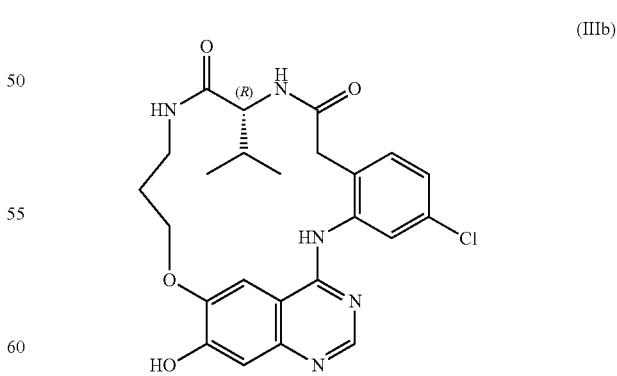

and isolating the resulting compound of formula (III).

In an alternative embodiment, the present invention provides a method for preparing a radiolabeled compound according to formula (II); said method comprising the step of reacting radiolabeled

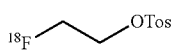

with a compound of formula (IIb)

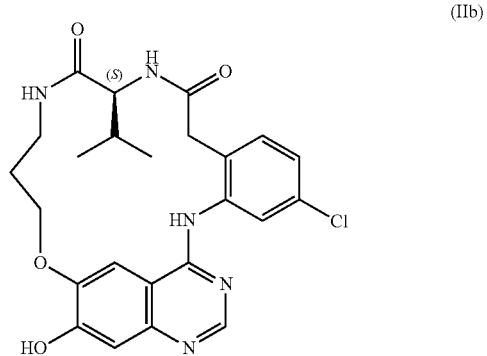

(IIb)

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
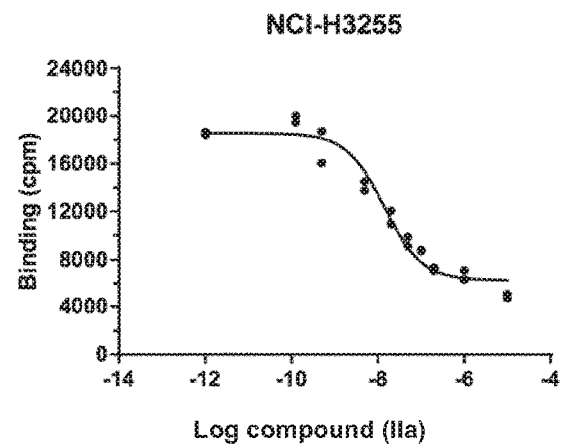
FIG. 1: Binding affinity constant of Compound (II) determined in competition experiments on NCI-H3255 (A) and NCI-H441 (B) cell line extracts. NCI-H3255 and NCI-H441 cell line extracts were incubated at room temperature for 90 min with Compound (II) (0.5-0.7 nM) and with increasing concentrations of Compound (IIa) (0.05 nM to 10 µM).
Figure 1:
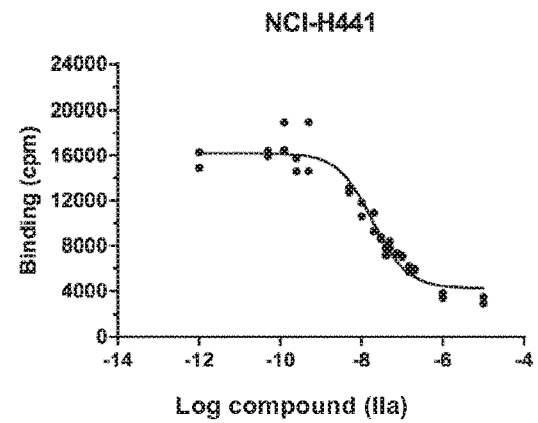

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula (I), or any prodrug, pharmaceutically acceptable salt, metabolite, polymorph, solvate, hydrate, stereoisomer, radioisotope or tautomer thereof

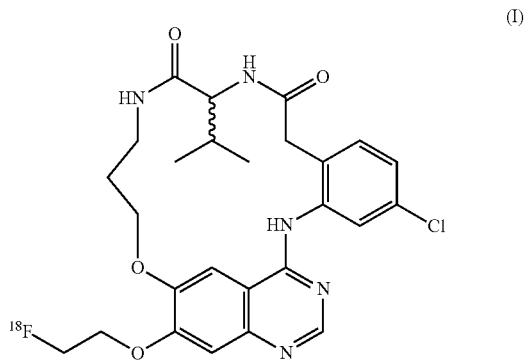 [SMILES: CC(C)C1NC(=O)Cc2ccc(Cl)cc2Nc2ncnc3cc(OCC[18F])c(cc23)OCCCNC1=O]

(I)

The compounds of the invention may contain one asymmetric carbon atom that serves as a chiral center, which may lead to different optical forms (e.g. enantiomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula (I), (II) or (III) (i.e. the radio-labeled compounds) and any subgroup thereof of Formula (Ia), (IIa) or (IIIa) (i.e. the 'cold' compounds). This term also refers to any prodrug, pharmaceutically acceptable salt, metabolite, polymorph, solvate, hydrate, stereoisomer, radioisotope or tautomer thereof. Compounds (Ib), (IIb) and (IIIb) are precursor compounds used in the preparation of compounds of the invention. An overview of the list of compounds of the invention, and precursor compounds can be found in table A.

TABLE A

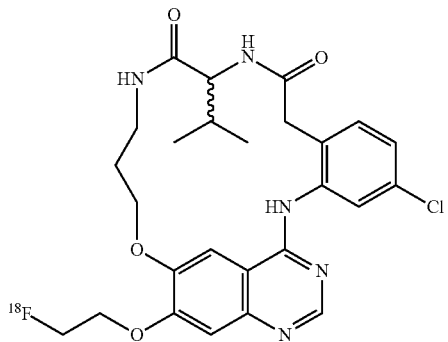 [SMILES: CC(C)C1NC(=O)Cc2ccc(Cl)cc2Nc2ncnc3cc(OCC[18F])c(cc23)OCCCNC1=O]

Compound I

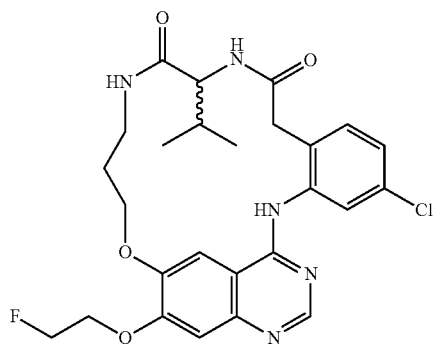 [SMILES: CC(C)C1NC(=O)Cc2ccc(Cl)cc2Nc2ncnc3cc(OCCF)c(cc23)OCCCNC1=O]

Compound Ia

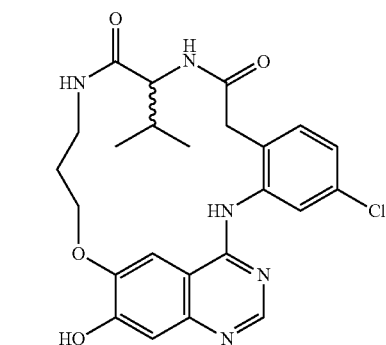 [SMILES: CC(C)C1NC(=O)Cc2ccc(Cl)cc2Nc2ncnc3cc(O)c(cc23)OCCCNC1=O]

Precursor Compound Ib

TABLE A-continued

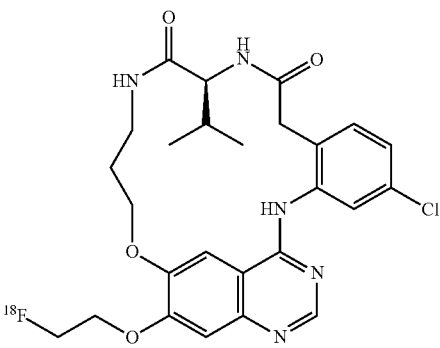 [SMILES: CC(C)[C@@H]1NC(=O)Cc2ccc(Cl)cc2Nc2ncnc3cc(OCC[18F])c(cc23)OCCCNC1=O]

Compound II

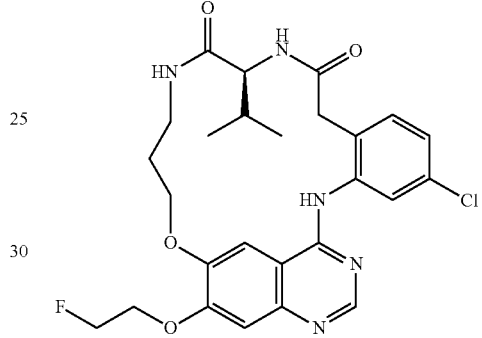

Compound IIa

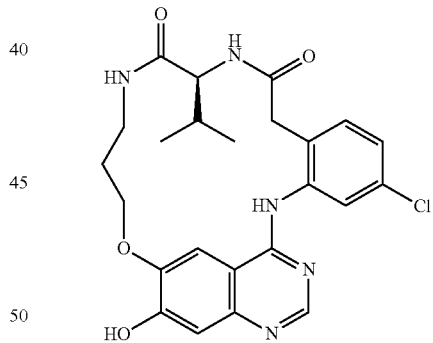 [SMILES: CC(C)[C@@H]1NC(=O)Cc2ccc(Cl)cc2Nc2ncnc3cc(OCCF)c(cc23)OCCCNC1=O]

Precursor Compound IIb

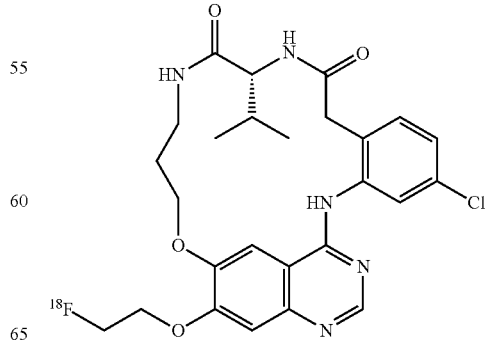

Compound III

TABLE A-continued

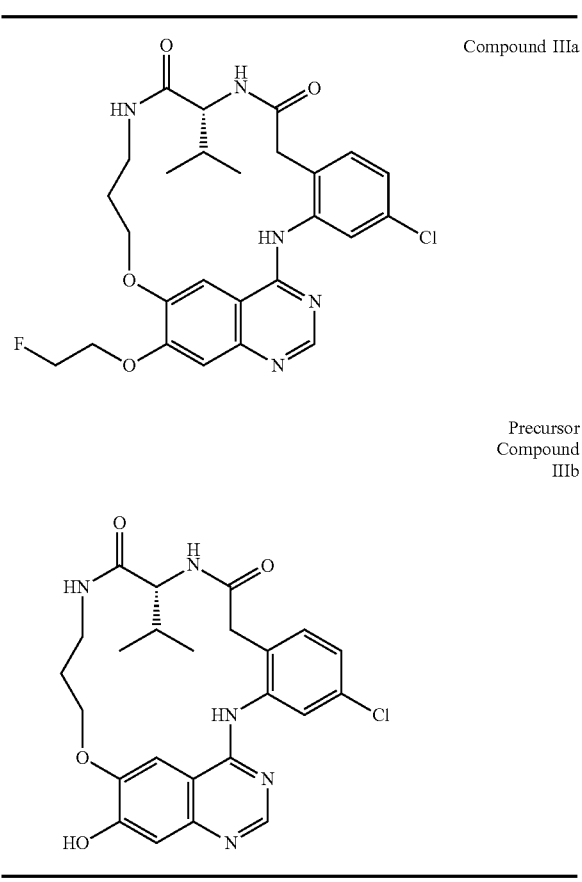

Compound IIIa

Precursor Compound IIIb

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a preferred embodiment, the present invention provides a compound of formula (III), i.e. being the R-enantiomer of the compound of formula (I)

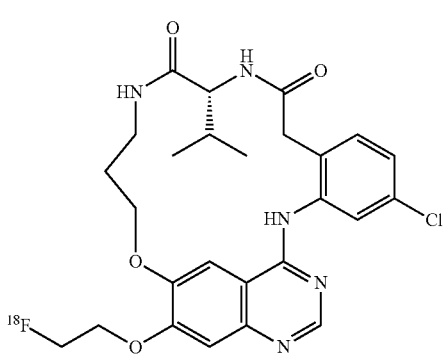
(III)

In an alternative embodiment, the present invention provides a compound of formula (II), i.e. being the S-enantiomer of the compound of formula (I)

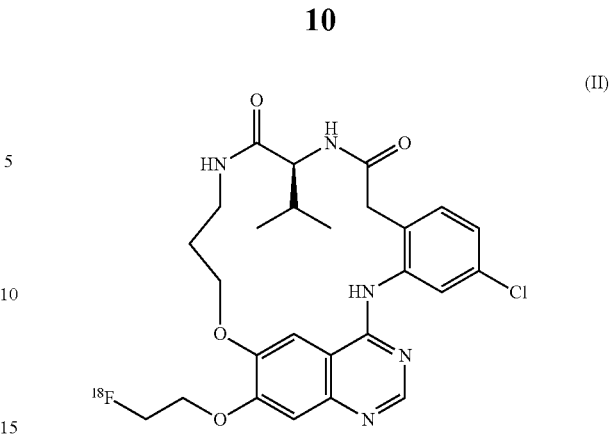
(II)

In a further aspect, the present invention provides a radiopharmaceutical composition comprising a radiolabeled compound according to anyone of formula (I), (II) or (III), optionally further comprising one or more inert carriers and/or diluent. In preferred embodiment, the present invention provides a radiopharmaceutical composition comprising a radiolabeled compound according to formula (II), optionally further comprising one or more inert carriers and/or diluent.

In yet a further aspect, the prevent invention provides the use of a radiolabeled compound according to anyone of formula (I), (II) or (III), or a radiopharmaceutical composition comprising a radiolabeled compound according to anyone of formula (I), (II) or (III); as a diagnostic agent in human medicine.

The present invention further provides the use of a radiolabeled compound according to anyone of formula (I), (II) or (III), or a radiopharmaceutical composition comprising a radiolabeled compound according to anyone of formula (I), (II) or (III); in tumor imaging.

In a further aspect, the present invention provides a method for in vivo diagnosis or tumor imaging comprising use of a radiolabeled compound according to anyone of formula (I), (II) or (III), or a radiopharmaceutical composition comprising a radiolabeled compound according to anyone of formula (I), (II) or (III).

In yet a further aspect, the present invention provides a method for diagnostic imaging of an EGFR-associated tumor in a human, which comprises administering to a human in need of such diagnostic imaging an effective amount of a compound according to anyone of formula (I), (II) or (III), or a radiopharmaceutical composition comprising a radiolabeled compound according to anyone of formula (I), (II) or (III); and obtaining an image useful for quantifying EGFR in the tumor of said human using positron emission tomography.

In a further aspect, the present invention provides a method for the quantification of EGFR in human tissue, which comprises contacting such human tissue in which quantification is desired with an effective amount of a compound according to anyone of formula (I), (II) or (III), or a radiopharmaceutical composition comprising a radiolabeled compound according to anyone of formula (I), (II) or (III); and detecting or quantifying EGFR using positron emission tomography.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Hence, in further aspect, the present invention provides a method for preparing a radiolabeled compound according to formula (I); said method comprising the step of reacting radiolabeled

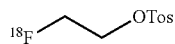

with a compound of formula (Ib)

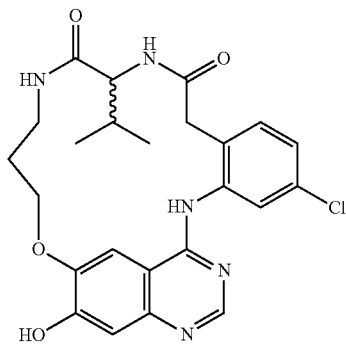

(Ib)

and isolating the resulting compound of formula (I).

In a preferred embodiment, the present invention provides a method for preparing a radiolabeled compound according to formula (II); said method comprising the step of reacting radiolabeled

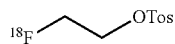

with a compound of formula (IIIb)

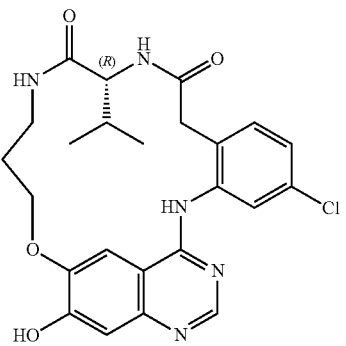

(IIIb)

and isolating the resulting compound of formula (III)

In an alternative embodiment, the present invention provides a method for preparing a radiolabeled compound according to formula (III); said method comprising the step of reacting radiolabeled

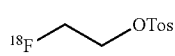

with a compound of formula (IIIb)

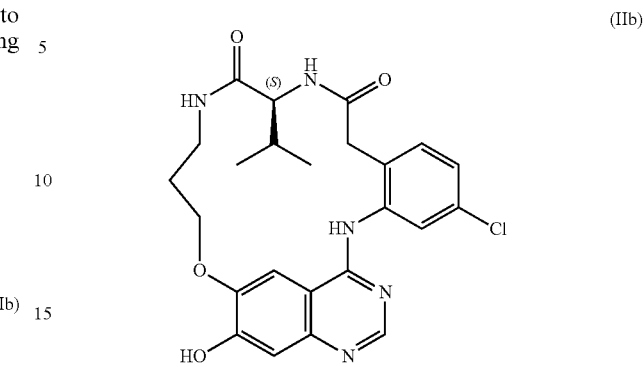

(IIb)

and isolating the resulting compound of formula (II)

Method of Diagnosis

The present invention provides a method for the diagnosis and treatment follow-up of cancer, more in particular at least one disease or disorder selected from but not limited to the group comprising non-small cell lung cancer, pancreatic, hepatocellular, oesophageal, gastric, colorectal, prostate, cervical, renal, ovarian, breast cancers, head and neck squamous cell carcinoma, and malignant glioma.

For diagnostic use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for diagnostic use, the compounds of the inventions may be formulated as a diagnostic preparation or radiopharmaceutical composition comprising at least one compound of the invention and at least one pharmaceutically acceptable carrier, diluent or excipient and/or adjuvant.

By means of non-limiting examples, such a formulation may be in a form suitable for parenteral administration (such as by intravenous infusion). Such suitable administration forms as well as methods and carriers, diluents and excipients for use in the preparation thereof, will be clear to the skilled person; reference is again made to for instance U.S. Pat. No. 6,372,778, 6,369,086, 6,369,087 and 6,372,733, as well as to the standard handbooks, such as the latest edition of Remington's Pharmaceutical Sciences.

Some preferred, but non-limiting examples of such preparations include sterile injectable solutions for administration as a bolus and/or for continuous administration, which may be formulated with carriers, excipients, and diluents that are suitable per se for such formulations. In addition, co-solvents such as alcohols may improve the solubility and/or the stability of the compounds. In the preparation of aqueous compositions, addition of salts of the compounds of the invention can be more suitable due to their increased water solubility.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. The compounds can be administered by intravenous route, The at least one compound of the invention will generally be administered in an "effective amount", by which is meant any amount of a compound of the Formula (I), (II) or (III) or any subgroup thereof that, upon suitable administration, is sufficient to allow diagnostic imaging in the individual to which it is administered. Usually, depending on the condition to be imaged, such an effective amount will usually be between 1-10 Mbq per kilogram body weight day of the patient per administration, more often between 3-5 Mbq/kg, per kilogram body weight day of the patient per day, which may be administered as a single daily dose, The amount(s) to be administered and the route of administration may be determined by the radiologist or nuclear physicist, depending on factors such as the age, gender and general condition of the patient.

The invention will now be illustrated by means of the following synthetic and biological examples, which do not limit the scope of the invention in any way.

EXAMPLES

Synthesis Routes

Preparation of the Precursor Compound Formula (IIb)

The preparation of precursor compound (IIb) is described in Scheme 1.

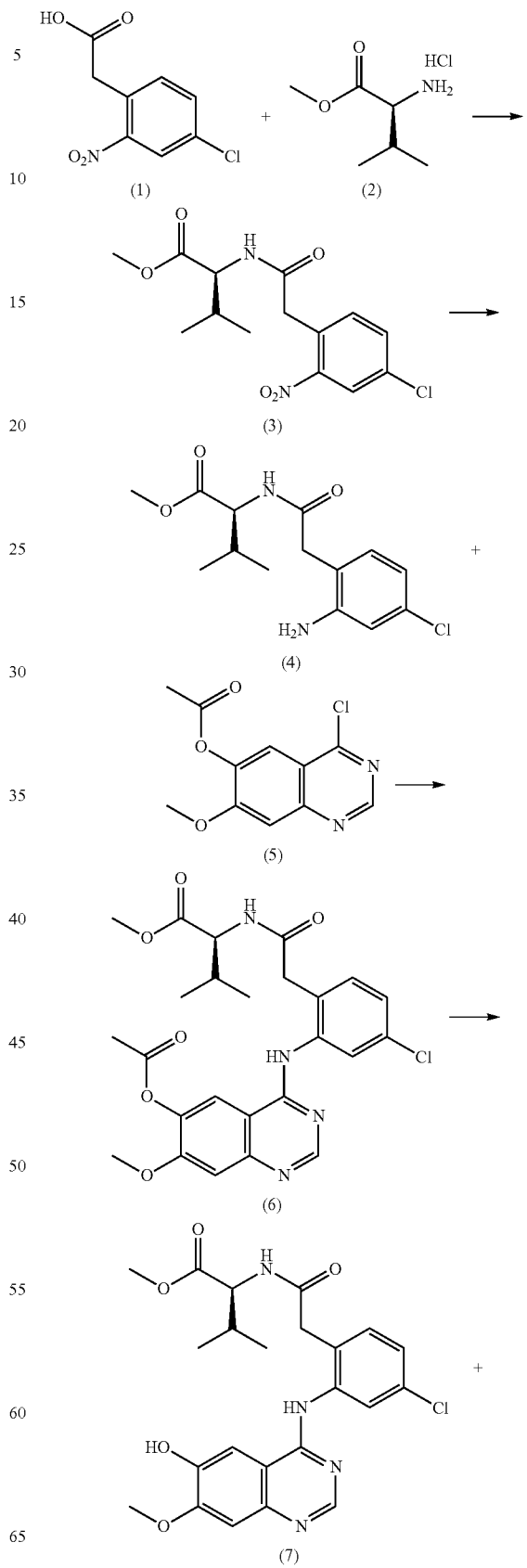

Scheme 1

-continued

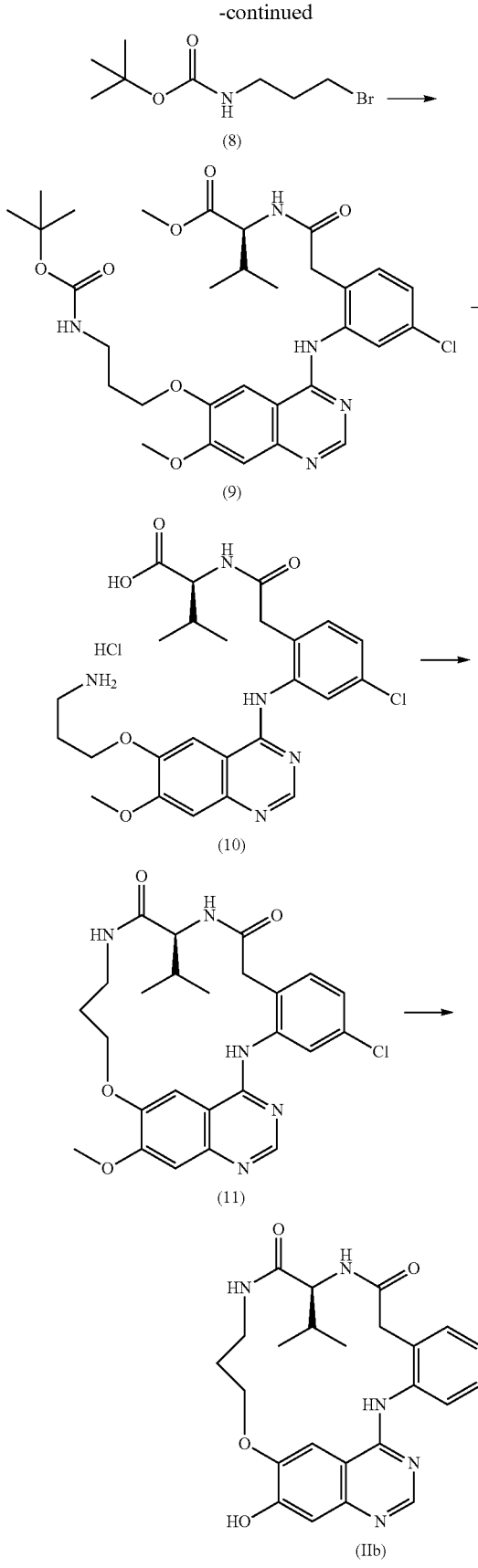

Following Scheme 1, starting from methyl (2S)-2-amino-3-methyl-butanoate, a mixture is obtained in which the S-enantiomer of formula (IIb) is the major occurring enantiomer. The S-enantiomer (IIb) can be separated from the R-enantiomer (IIIb) by chiral HPLC.

Intermediate (3)

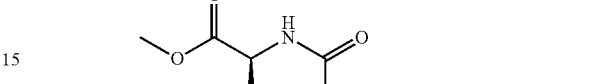

To a stirred solution of 2-(4-chloro-2-nitro-phenyl)acetic acid (10.0 g, 46.38 mmol) and methyl (2S)-2-amino-3-methyl-butanoate; hydrochloride (7.78 g, 46.38 mmol) in acetonitrile (139 ml) were added O-(benzotriazol-1-yl)-N,N,N',N'-tetramethyluronium hexafluorophosphate (21.11 g, 55.66 mmol) and N,N-diisoproylethylamine (23.42 ml, 139.14 mmol). The mixture was stirred at room temperature overnight. Ethyl acetate was added and the organic layer was washed with a saturated aqueous sodium bicarbonate solution. The organic layer was dried, filtered and the solvent was removed under reduced pressure. The product was used in the next step without further purification.

Intermediate (4)

lp;2p

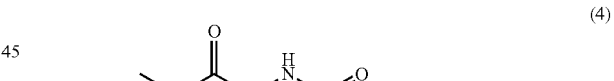

A mixture of intermediate (3) (46.38 mmol), iron (12.95 g, 231.90 mmol) and ammonium chloride (24.81 g, 463.80 mmol) in toluene, tetrahydrofuran and water (450 ml) was stirred under reflux overnight. The reaction mixture was cooled, filtered and the residue was washed with a mixture of tetrahydrofuran and methanol (4:1). The solvent of the filtrate was removed under reduced pressure. Ethyl acetate was added and the organic layer was washed with a saturated aqueous sodium bicarbonate solution. The organic layer was dried, filtered and the solvent was removed under reduced pressure. The residue was purified by flash column chromatography over silica gel.

Yield: 12.0 g of intermediate (4) (87%)
LCMS method 1: MH+=299, RT=0.763 min

Intermediate (6)

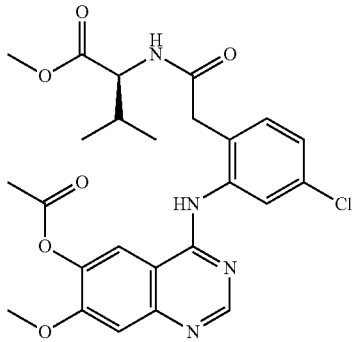

(6)

A mixture of (4-chloro-7-methoxy-quinazolin-6-yl) acetate (10.02 g, 39.66 mmol) and intermediate (4) (11.85 g, 39.66 mmol) in isopropanol (119 ml) was stirred at 80° C. for 5 hours. The mixture was cooled and the solvent was removed under reduced pressure. Ethyl acetate was added and the organic layer was washed with a saturated aqueous sodium bicarbonate solution. The organic layer was dried, filtered and the solvent was removed under reduced pressure. The product was used in the next step without further purification.

Yield: 9.64 g of intermediate (6) (47%)
LCMS method 1: MH+=492, RT=0.430 min

Intermediate (7)

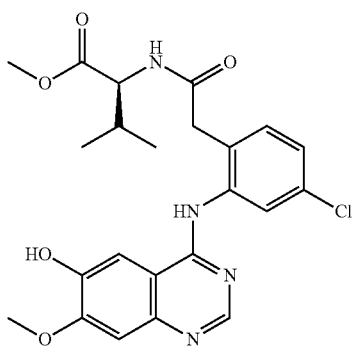

(7)

Ammonia in methanol (7N) (38 ml) was added to a solution of intermediate (6) (13.87 g, 26.93 mmol) in methanol (110 ml). The reaction mixture was stirred at room temperature for 48 hours. Ethyl acetate was added and the organic layer was washed with brine. The organic layer was dried, filtered and the solvent was removed under reduced pressure. The product was used in the next step without further purification.

LCMS method 1: MH+=473, RT=0.618 min

Intermediate (9)

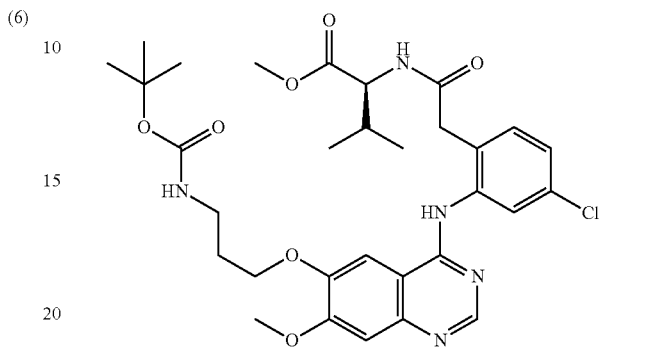

(9)

Cesium carbonate (9.36 g, 28.74 mmol) was added to a solution of intermediate (7) (9.06 g, 19.16 mmol) in dry N,N-dimethylformamide (57.5 ml) and the mixture was stirred at room temperature for 1 hour. Tert-butyl N-(3-bromopropyl)carbamate (5.02 g, 21.08 mmol) was added and the reaction mixture was stirred at room temperature overnight. Ethyl acetate was added and the organic layer was washed with a saturated aqueous sodium bicarbonate solution. The organic layer was dried, filtered and the solvent was removed under reduced pressure. The product was used in the next step without further purification.

Yield: 11.48 g of intermediate (9) (95%)
LCMS method 1: MH+=630, RT=0.877 min

Intermediate (10)

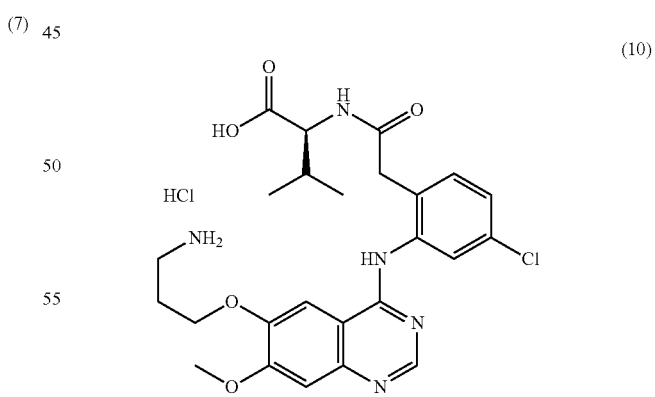

(10)

Intermediate (9) (11.48 g, 18.22 mmol) was dissolved in 1,4-dioxane (227 ml) and a 12N hydrochloric acid solution (45.5 ml, 546.60 mmol) was added. The reaction mixture was stirred at 60° C. for 3 hours. The solvent was removed under reduced pressure. The residue was washed with diethyl ether and dried under reduced pressure. The product was used in the next step without further purification.

LCMS method 1: MH⁺=517, RT=0.366 min

Intermediate (11)

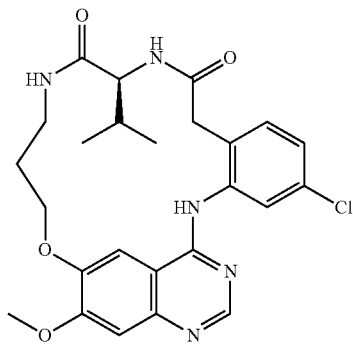

(11)

A solution of intermediate (10) (3.30 g, 5.97 mmol) in N,N-dimethylformamide (100 ml) was added over a period of 2 hours to a solution of O-(benzotriazol-1-yl)-N,N,N',N'-tetramethyluronium hexafluorophosphate (4.98 g, 13.13 mmol) and N,N-diisopropylethylamine (30.5 ml, 179.16 mmol) in N,N-dimethylformamide (200 ml). The reaction mixture was stirred at room temperature for 30 minutes. The solvent was removed under reduced pressure. Dichloromethane was added and the organic layer was washed with a saturated aqueous sodium bicarbonate solution. The aqueous layer was washed with dichloromethane. The combined organic layers were dried, filtered and the solvent was removed under reduced pressure. The crude product was purified by crystallization from acetonitrile.

Yield: 1.55 g of intermediate (11) (52%)
LCMS method 1: MH⁺=498, RT=0.581 min

Intermediate (IIb)

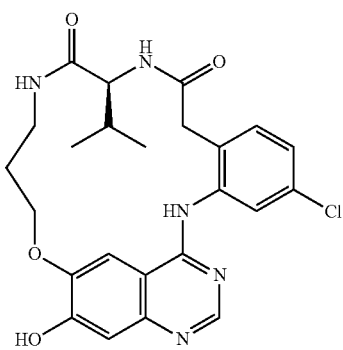

(IIb)

The experiment was done in 6 batches on 0.3 g of intermediate (11) each.

Water (2 drop/ml N,N-dimethylacetamide) was added drop wise to a mixture of intermediate (11) (0.3 g, 0.60 mmol), lithium chloride (0.25 g, 5.90 mmol) and disodium sulphide (0.515 g, 6.60 mmol) in N,N-dimethylacetamide (8 ml). The reaction mixture was stirred at room temperature for 30 minutes and at 140° C. for 4 hours. Ethyl acetate was added and the organic layer was washed with a saturated aqueous sodium bicarbonate solution. The aqueous layer was washed with ethyl acetate. The combined organic layers were dried, filtered and the solvent was removed under reduced pressure. The crude product was purified by crystallization from acetonitrile.

Yield: 2.22 g of intermediate (IIb) (85%)
LCMS method 2: MH⁺=484, RT=2.000 min

Preparation of the Cold Analogue (IIa)

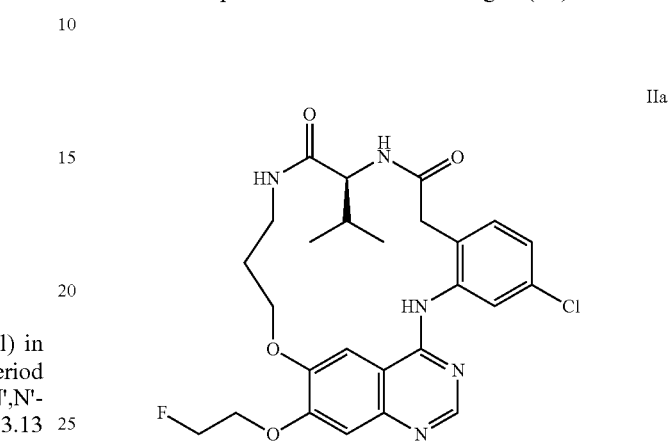

IIa

To a solution of intermediate (IIb) (110 mg, 0.23 mmol) in dry N,N-dimethylformamide (4.0 ml) was added cesium carbonate (91 mg, 0.28 mmol). The mixture was stirred at room temperature for 1 hour. A solution of 1-fluoro-2-iodo-ethane (260 mg, 1.5 mmol) in dry N,N-dimethylformamide (1.0 ml) was added and the mixture reaction was stirred at room temperature overnight. Ethyl acetate was added and the organic layer was washed with a saturated aqueous sodium bicarbonate solution. The organic layer was dried, filtered and the solvent was removed under reduced pressure. The residue was purified by flash column chromatography over silica gel.

Yield: 54 mg of compound (IIa) (44%), purity=99%
LCMS method 2: MH⁺=530, RT=2.443 min Chiral separation of the two enantiomers can be achieved either on the precursor compound (IIb) or on the cold analogue (IIa). As an example, but not limiting, the chiral separation of a 30/70 R/S mixture of a compound of formula (IIb) has been described.

Chiral Separation of Precursor Compound with Formula (IIb):

Preparative Method:

Column: CHIRALPAK® IA 5 μm-250×30 mm

Mobile phase: Carbon Dioxide/(Ethanol+1% Diethylamine) 60/40

Flow rate: 120 ml/min

Detection: UV 230 nm

Outlet Pressure: 120 bar

Temperature: 25° C.

Analytical Method:

Column: CHIRALPAK® AD-H 5 μm-250×4.6 mm

Mobile phase: n-Heptane/Ethanol/Ethylenediamine 80/20/0.1

Flow rate: 1 ml/min

Detection: DAD 300 nm

Temperature: 25° C.

Results:

From 420 mg of crude material:

| First eluting enantiomer Pure (R)-enantiomer (IIb) | Second eluting enantiomer Pure (S)-enantiomer (IIIb) |
|---|---|
| Retention time (min) = 4.5 | Retention time (min) = 5.9 |
| Quantity (mg) = 38 | Quantity (mg) = 313 |
| Chemical purity (area % at 314 nm) = 99.3 | Chemical purity (area % at 314 nm) > 99.5 |
| Enantiomeric excess (%) = 99.2 | Enantiomeric excess (%) = 99.0 |

The pure enantiomers can be used to perform the alkylation step (cold or with $^{18}$F).

The (R)-enantiomer analogues of intermediate (IIIb) and compound (IIIa) can be prepared according to the experimental procedures described above.

Preparation of the Precursor Compound Formula (IIIb)

The preparation of precursor compound (IIIb) is described in Scheme 2.

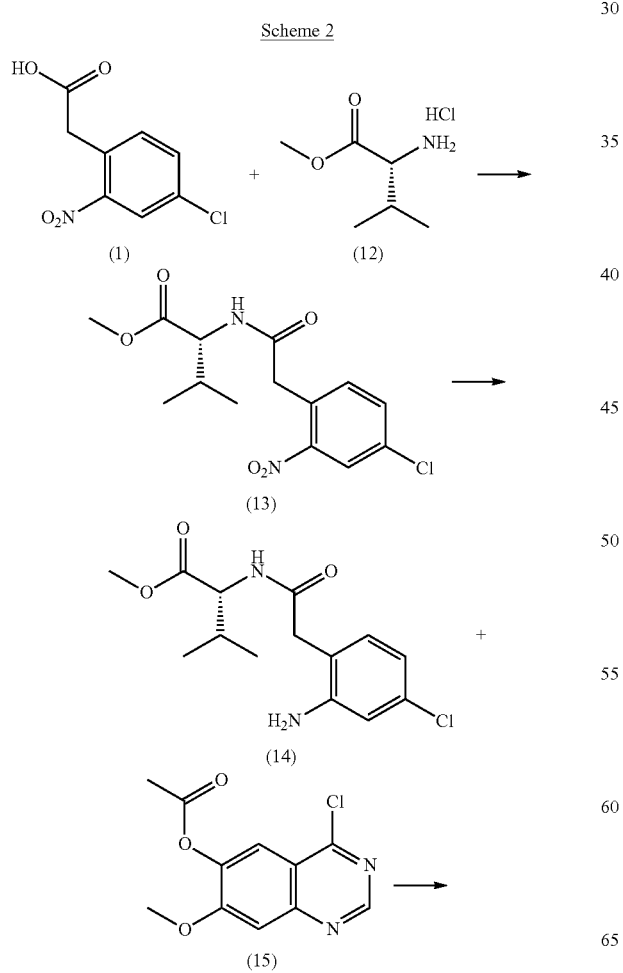

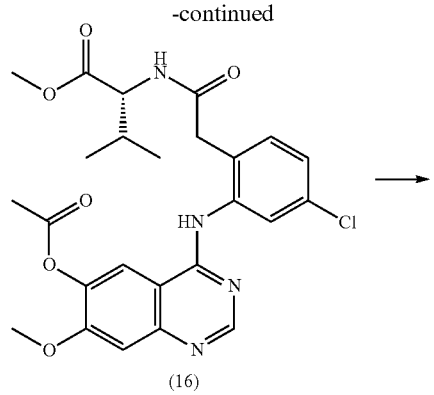

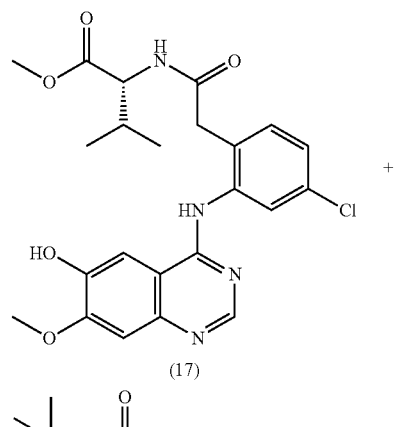

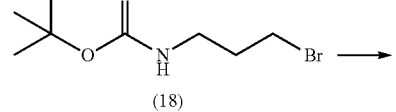

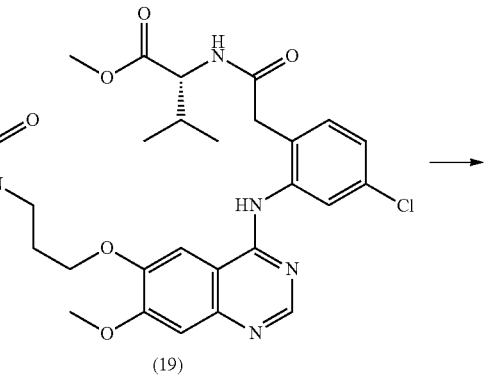

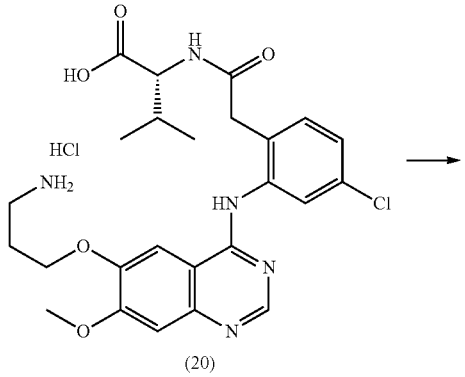

-continued

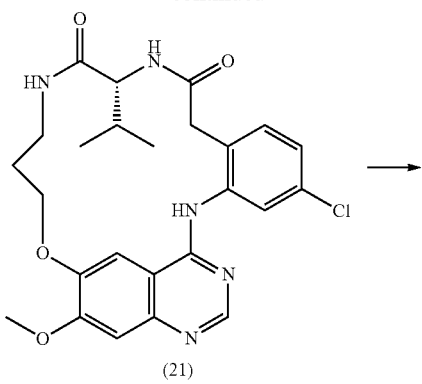

(21)

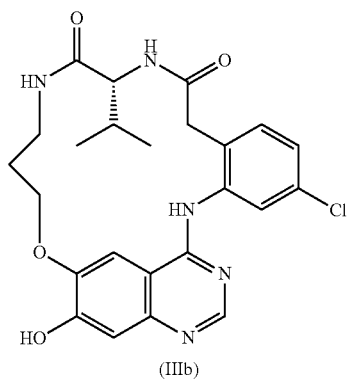

(IIIb)

Following Scheme 2, starting from methyl (2R)-2-amino-3-methyl-butanoate, a mixture is obtained in which the R-enantiomer of formula (IIIb) is the major occurring enantiomer. The R-enantiomer (IIIb) can be separated from the S-enantiomer (IIb) by chiral HPLC.

Intermediate (13)

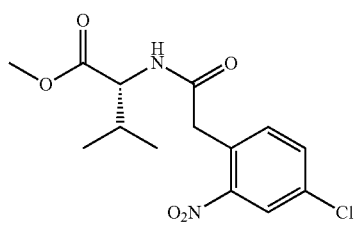

(13)

To a stirred solution of 2-(4-chloro-2-nitro-phenyl)acetic acid (12.86 g, 59.65 mmol) and methyl (2R)-2-amino-3-methyl-butanoate; hydrochloride (10.0 g, 59.65 mmol) in acetonitrile (179 ml) were added O-(benzotriazol-1-yl)-N,N,N',N'-tetramethyluronium hexafluorophosphate (27.147 g, 71.58 mmol) and N,N-diisopropylethylamine (31.172 ml, 178.95 mmol). The mixture was stirred at room temperature overnight. Ethyl acetate was added and the organic layer was washed with a saturated aqueous sodium bicarbonate solution. The organic layer was dried, filtered and the solvent was removed under reduced pressure. The product was used in the next step without further purification.

Intermediate (14)

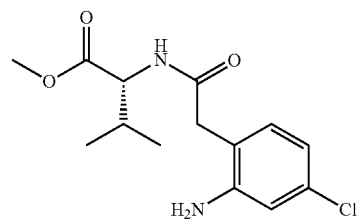

(14)

A mixture of intermediate (13) (59.65 mmol), iron (16.66 g, 298.95 mmol) and ammonium chloride (31.907 g, 596.5 mmol) in toluene, tetrahydrofuran and water (1:1:1, 450 ml) was stirred under reflux overnight. The reaction mixture was cooled, filtered and the residue was washed with a mixture of tetrahydrofuran and methanol (4:1). The solvent of the filtrate was removed under reduced pressure. Ethyl acetate was added and the organic layer was washed with a saturated aqueous sodium bicarbonate solution. The organic layer was dried, filtered and the solvent was removed under reduced pressure. The residue was purified by flash column chromatography over silica gel.

Yield: 16.5 g of intermediate (14) (93%)

Intermediate (16)

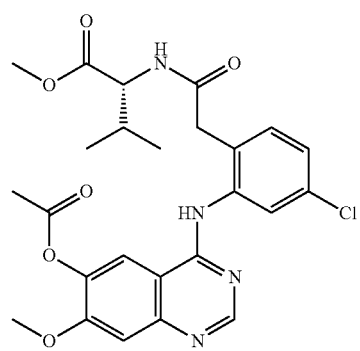

(16)

A mixture of (4-chloro-7-methoxy-quinazolin-6-yl) acetate (9.553 g, 37.81 mmol) and intermediate (14) (11.30 g, 37.81 mmol) in isopropanol (113.4 ml) was stirred at 80° C. for 5 hours. The mixture was cooled and the solvent was removed under reduced pressure. Ethyl acetate was added and the organic layer was washed with a saturated aqueous sodium bicarbonate solution. The organic layer was dried, filtered and the solvent was removed under reduced pressure. The product was used in the next step without further purification.

Yield: 19 g of intermediate (16) (98%)
LCMS method 1: MH⁺=515, RT=1.209 min

Intermediate (17)

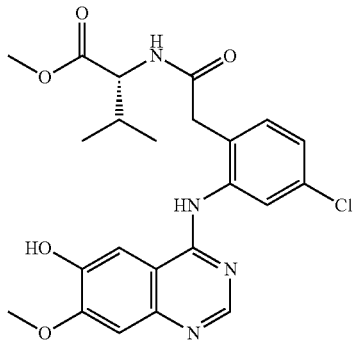

Ammonia in methanol (7N) (60 ml) was added to a solution of intermediate (16) (19.00 g, 36.90 mmol) in methanol (110.7 ml). The reaction mixture was stirred at room temperature for 48 hours. Ethyl acetate was added and the organic layer was washed with brine. The organic layer was dried, filtered and the solvent was removed under reduced pressure. The product was used in the next step without further purification.

Yield: 13.6 g of intermediate (17) (78%)

Intermediate (19)

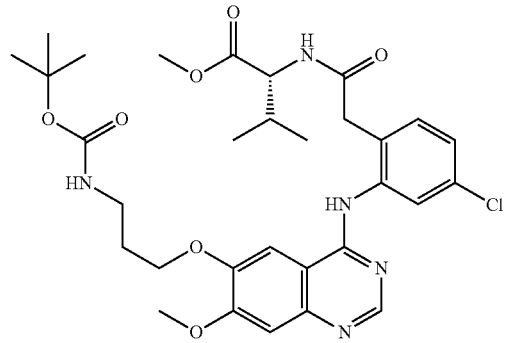

Cesium carbonate (14.056 g, 43.14 mmol) was added to a solution of intermediate (17) (13.60 g, 28.76 mmol) in dry N,N-dimethylformamide (86.3 ml) and the mixture was stirred at room temperature for 1 hour. Tert-butyl N-(3-bromopropyl)carbamate (6.85 g, 28.76 mmol) was added and the reaction mixture was stirred at room temperature overnight. Ethyl acetate was added and the organic layer was washed with a saturated aqueous sodium bicarbonate solution. The organic layer was dried, filtered and the solvent was removed under reduced pressure. The residue was purified by flash column chromatography over silica gel using heptane and ethyl acetate as eluents.

Yield: 3.05 g of intermediate (19) (17%)
LCMS method 1: MH⁺=630, RT=1.474 min

Intermediate (20)

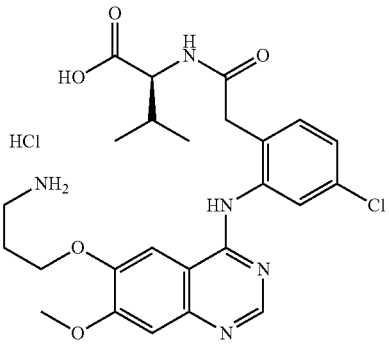

Intermediate (19) (2.635 g, 4.18 mmol) was dissolved in 1,4-dioxane (55 ml) and a 12N hydrochloric acid solution (10.9 ml, 125.40 mmol) was added. The reaction mixture was stirred at 60° C. for 3 hours. The solvent was removed under reduced pressure. The residue was washed with diethyl ether and dried under reduced pressure. The product was used in the next step without further purification.

Intermediate (21)

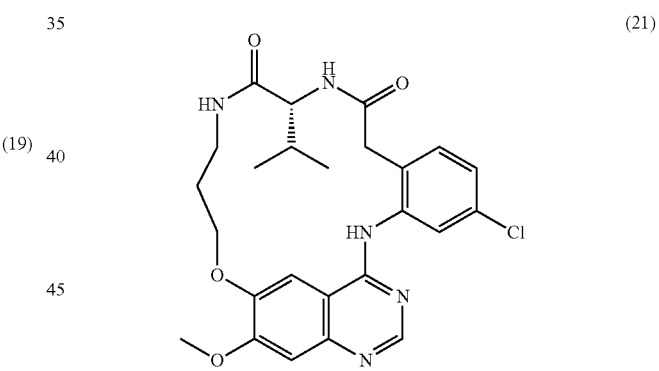

A solution of intermediate (20) (3.05 g, 5.52 mmol) in N,N-dimethylformamide (150 ml) was added over a period of 2 hours to a solution of O-(benzotriazol-1-yl)-N,N,N',N'-tetramethyluronium hexafluorophosphate (2.09 g, 5.52 mmol) and N,N-diisopropylethylamine (28.163 ml, 165.60 mmol) in N,N-dimethylformamide (250 ml). The reaction mixture was stirred at room temperature for 30 minutes. A solution of ammonia (7 N solution in methanol, 2 ml)) was added and the mixture was stirred at room temperature for 30 minutes. The solvent was removed under reduced pressure. Dichloromethane was added and the organic layer was washed with a saturated aqueous sodium bicarbonate solution. The aqueous layer was extracted with dichloromethane. The combined organic layers were dried, filtered and the solvent was removed under reduced pressure. The residue was purified by flash column chromatography over silica gel using dichloromethane and methanol (20%) as eluents. The product fractions were collected and the solvent was removed under reduced pressure. The product was triturated with methanol, filtered and the solid was dried under reduced pressure.

Yield: 750 mg of intermediate (21) (27%)

Intermediate (IIIb)

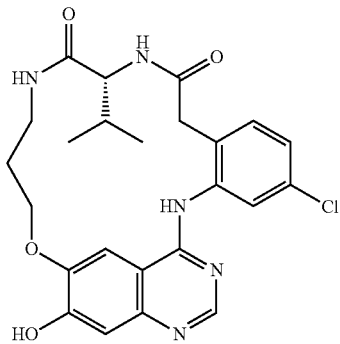

(IIIb)

The experiment was done in 9 batches on 0.3 g of intermediate (21) each.

Water (2 drop/ml N,N-dimethylacetamide) was added drop wise to a mixture of intermediate (21) (0.3 g, 0.60 mmol), lithium chloride (0.25 g, 6.00 mmol) and disodium sulphide (0.515 g, 6.60 mmol) in N,N-dimethylacetamide (8 ml). The reaction mixture was stirred at room temperature for 30 minutes and at 140° C. for 4 hours. More disodium sulphide (0.4 eq.) was added and the reaction mixture was stirred at 140° C. for 1 hour. Ethyl acetate was added and the organic layer was washed with a saturated aqueous sodium bicarbonate solution. The aqueous layer was extracted with ethyl acetate. The combined organic layers were dried, filtered and the solvent was removed under reduced pressure. The crude product was purified by crystallization from acetonitrile, the solid was filtered and washed with diethyl ether. The compound was dried under reduced pressure.

Yield: 164 mg of intermediate (IIIb) (56%)

Preparation of the Cold Analogue (IIIa)

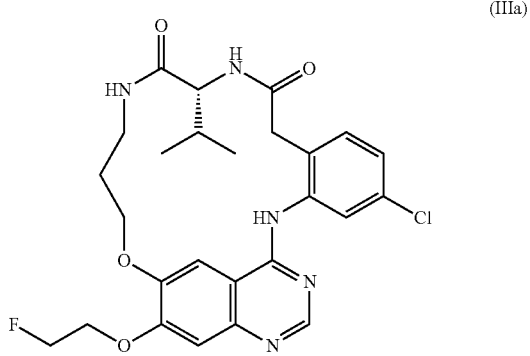 [SMILES: CC(C)[C@H]1NC(=O)Cc2ccc(Cl)cc2Nc2ncnc3cc(OCCF)c(cc23)OCCCNC1=O]

(IIIa)

To a solution of intermediate (IIIb) (156 mg, 0.32 mmol) in dry N,N-dimethylformamide (5.0 ml) was added cesium carbonate (124 mg, 0.38 mmol). The mixture was stirred at room temperature for 1 hour. A solution of 1-fluoro-2-iodo-ethane (110 mg, 0.64 mmol) in dry N,N-dimethylformamide (1.0 ml) was added and the mixture reaction was stirred at room temperature overnight. Ethyl acetate was added and the organic layer was washed with a saturated aqueous sodium bicarbonate solution. The organic layer was dried, filtered and the solvent was removed under reduced pressure. The residue was purified by flash column chromatography over silica gel. The product was triturated with diethyl ether, filtered and dried under reduced pressure.

Yield: 95 mg of compound (IIIa) (56%)

LCMS method 2: MH$^+$=530, RT=2.537 min

Chiral separation of the two enantiomers can be achieved either on the precursor compound (IIIb) or on the cold analogue (IIIa). As an example, but not limiting, the chiral separation of a 70/30 R/S mixture of a compounds of formula (IIIa) has been described.

Chiral Separation of Compound with Formula (IIIa):
Preparative Method:
Column: CHIRALPAK®AD-H 5 μm-250×30 mm
Mobile phase: Ethanol/Methanol 50/50
Flow rate: 30 mL/min
Detection: UV 250 nm
Temperature: 25° C.
Analytical Method:
Column: CHIRALPAK® IA 5 μm-250×4.6 mm
Mobile phase: Heptane/Isopropanol/Ethylendiamine 50/50/0.1
Flow rate: 1 mL/min
Detection: DAD 336 nm
Temperature: 35° C.
Samples dissolved in 100% Ethanol
Results:
From 141 mg of crude material (IIIa):

| First eluting enantiomer Pure (R)-enantiomer (IIIa) | Second eluting enantiomer Pure (S)-enantiomer (IIa) |
|---|---|
| Retention time (min) = 3.7 | Retention time (min) = 5.6 |
| Quantity (mg) = 90 | Quantity (mg) = 42 |
| Chemical purity (area % at 314 nm) > 99.5 | Chemical purity (area % at 314 nm) > 99.5 |
| Enantiomeric excess (%) > 99.5 | Enantiomeric excess (%) = 98.8 |

Compound Identification
LCMS

For LCMS-characterization of the compounds of the present invention, the following method was used.
General Procedure LCMS All analyses were performed using an Agilent 6110 series LC/MSD quadrupole coupled to an Agilent 1290 series liquid chromatography (LC) system consisting of a binary pump with degasser, auto sampler, thermostated column compartment and diode array detector. The mass spectrometer (MS) was operated with an atmospheric pressure electro-spray ionization (API-ES) source in positive ion mode. The capillary voltage was set to 3000 V, the fragmentor voltage to 70 V and the quadrupole temperature was maintained at 100° C. The drying gas flow and temperature values were 12.0 L/min and 350° C. respectively. Nitrogen was used as the nebulizer gas, at a pressure of 35 psig. Data acquisition was performed with Agilent Chemstation software.
LCMS Method 1

In addition to the general procedure LCMS1: Analyses were carried out on a Phenomenex Kinetex C18 column (50 mm long×2.1 mm i.d.; 1.7 μm particles) at 60° C., with a flow rate of 1.5 mL/min. A gradient elution was performed from 90% (water+0.1% formic acid)/10% Acetonitrile to 10% (water+0.1% formic acid)/90% acetonitrile in 1.50 minutes, then the final mobile phase composition was held for an additional 0.40 min. The standard injection volume was 2 μL. Acquisition ranges were set to 254 nm for the UV-PDA detector and 80-800 m/z for the MS detector.
LCMS Method 2

In addition to the general procedure LCMS1: Analyses were carried out on a YMC pack ODS-AQ C18 column (50 mm long×4.6 mm i.d.; 3 μm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

Preparation of the Radiolabeled Final Compound (II)

The preparation of the final radiolabeled compound (II) is described in Scheme 3.

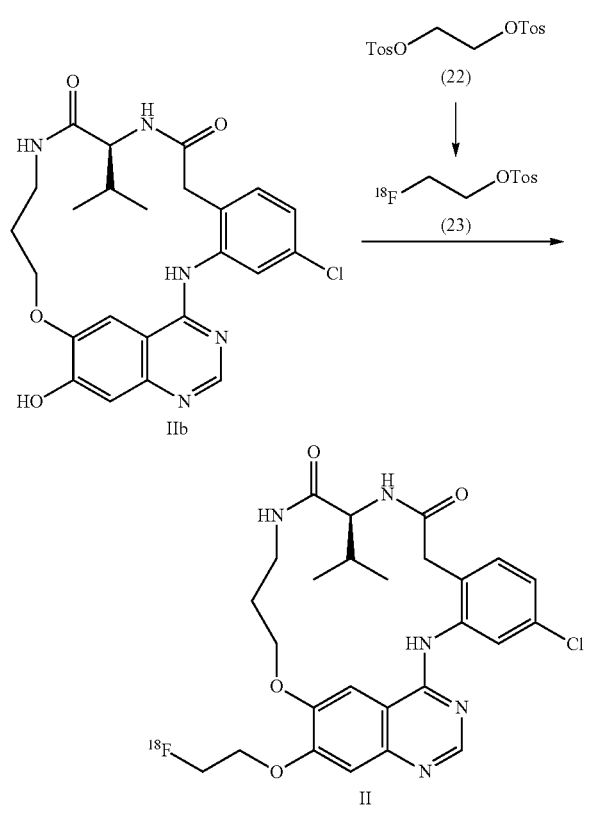

The synthesis of the radiolabeled compounds is performed on an automatic synthesizer (TracerLab FX-FN Pro, GE Healthcare).
Radiolabeled Intermediate (23) [$^{18}$F]Fluoroethyltosylate:

No-carrier-added aqueous 18F-fluoride ion was produced on a cyclotron (PET trace, GE Healthcare) by irradiation of enriched $^{18}$O H$_2$O with protons via the $^{18}$O (p,n)18F nuclear reaction. 18F-Fluoride was transferred to a GE TRACERlab FX-FN synthesizer and passed through an anion-exchange resin (Waters Sep-Pak Accell Light QMA cartridge in the carbonate form). Trapped 18F-fluoride was isolated by elution with a solution of aqueous eluent solution containing K$_2$CO$_3$ (7 mg in 300 μL of pure water), acetonitrile (300 μL), and 22 mg of Kryptofix-$_{222}$ (4,7,13,16,21,24-hexaoxa-1,10-diazabicyclo [8.8.8] hexacosane). Azeotropic drying by addition of ACN (1 mL) was performed. The evaporation was performed at 90° C. under helium flow and vacuum, and the operation was repeated twice.

The ethylene ditosylate (10 mg in 350 μL of ACN) was added to reactor 1 containing the fluoride. The reactor was heated at 90° C. for 7 min and then cooled to 30° C. [$^{18}$F]Fluoroethyltosylate was purified on silica cartridge (Sep Pak Plus, WAT020520, Waters) conditioned with dichloromethane (DCM) and Cyclohexane (5 mL, 5/5:v/v). 2 mL of DCM/Cyclohexane (5/5:v/:v) were added to the reactor. The mixture was passed through the cartridge and eluate sent to waste. The [$^{18}$F]Fluoroethyltosylate was eluated from the cartridge using 1.5 mL of DCM/Cyclohexane (7/3:v/:v) to reactor 2. Solvents were removed under atmospheric pressure by heating under a helium flow. The same operation was repeated once.
Radiolabeled Final Compound (II)

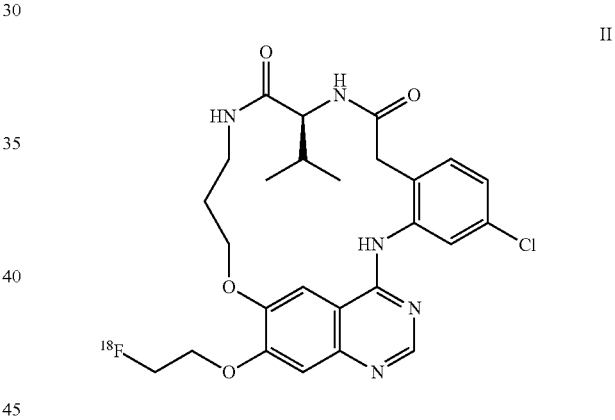

In reactor 2 of the FX-FN Pro module containing the dried [$^{18}$F]Fluoroethyltosylate was added the intermediate IIb (3 mg in 400 μL of DMSO) with 2.8 mg of cesium carbonate (2.8 mg in 20 μL of water). The reactor was put under pressure and heated at 100° C. for 20 min. Then reactor was cooled to 30-35° C. and 1.5 mL of ammonium acetate (0.1 M)/ACN (6/4:v/v) was added to dilute the crude solution. The solution was loaded onto the loop and purified by the HPLC integrated to the FX-FN Pro module. Purification occurred on an Agilent XDB C18 5 μm 9.4×250 mm column with ammonium acetate (0.1 M)/ACN (6/4: v/v) as mobile phase and a flow of 4 mL/min. In these conditions time retention is around 16 min. The collected fraction was diluted with 30 mL of water and passed through a tC18 light cartridge (Waters). The cartridge was rinsed with 5 mL of water and the final radiolabeled compound was eluted from the cartridge by using 500 μL of injectable ethanol. Formulation was completed by adding 3.5 mL of physiological serum.

By this method, the final radiolabeled compound can be obtained with a radiochemical purity greater than 98% in 100-110 min with a yield that can reach 25% (decay corrected). It has been noticed that an uncompleted evaporation of the solvents used for the purification of [$^{18}$F] Fluoroethyltosylate hampers the second step and conducts to lower yields. Specific activity of productions was in the range of 70-150 GBq/pmole. The radiolabeled compound is stable in the conditions of formulation as radiochemical purity still greater than 95% 20 h after production with a storage at room temperature. Plasmatic stability was also checked up to 4 h without significant degradation of the product.

The (R)-enantiomer radiolabelled compound of formula (III), can be prepared according to the experimental procedures described above.

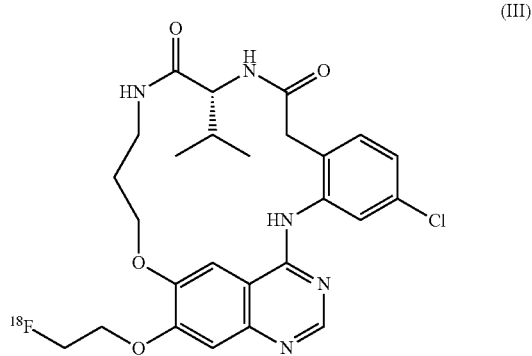 [SMILES: CC(C)[C@H]1NC(=O)Cc2ccc(Cl)cc2Nc2ncnc3cc(OCC[18F])c(cc23)OCCCNC1=O]

(III)

In Vitro and In Vivo Assays

Unless specifically stated, the in vitro and in vivo assays have been performed using a mixture of R (30%) and S (70%) compound.

Determination of Biochemical IC$_{50}$ and Selectivity Profile

A radiometric protein kinase assay ($^{33}$PanQinase® Activity Assay) was used for measuring the biochemical kinase activity of 3 protein kinases, EGFR wild-type and 2 EGFR mutants (L858R, L858R/T790M). The compounds were tested in 100% DMSO, all recombinant protein kinases and substrates with respective concentration are described in table 1.

TABLE 1

Recombinant protein kinases and substrates used for the biochemical kinase activity assays

| Kinase | | ATP Conc. | Substrate | |
|---|---|---|---|---|
| Name | Conc. nM | µM | Name | µg/50 µl |
| EGFR L858R (human, 672-1210) | 4.5 | 1.0 | poly(Glu, Tyr)4:1 | 0.25 |
| EGFR T790M/L858R (human, 672-1210) | 2.2 | 0.3 | poly(Glu, Tyr)4:1 | 0.125 |
| EGFR wt (human, 672-1210) | 4.4 | 0.3 | poly(Glu, Tyr)4:1 | 0.125 |

Compound (IIa) and Gefitinib, used as reference compound targeting EGFR (wild-type and L858R mutant but not L858R/T790M) were profiled against the 3 forms of EGFR. Activity of Compound (IIa) against EGFR WT and EGFR L858R mutant was below 10 nM, in the same range than gefitinib (Table 2). On the other hand, the biochemical activity against EGFR L858R/T790M double mutant was improved compared to gefitinib.

TABLE 2a

Biochemical activities in nM of Compound Ia compared to gefitinib

| Biochemical IC$_{50}$ (nM) | Compound (Ia)-Test 1 | Compound (Ia)-Test 2 | Compound (Ia)-Test 3 | Gefitinib |
|---|---|---|---|---|
| EGFR WT (activated) | 3.2 | 5 | 5.7 | 1.35 |
| EGFR L858R | 3 | 8 | 4.1 | 1.8 |
| EGFR L858R/T790M | 372 | 990 | 246 | 1350 |

TABLE 2b

Biochemical activities in nM of Compound (IIa) and (IIIa) after chiral separation

| Biochemical IC$_{50}$ (nM) | Compound (IIa)- Pure (S)- enantiomer- Test 1 | Compound (IIIa)- Pure (R)- enantiomer- Test 1 |
|---|---|---|
| EGFR WT (activated) | 5.9 | 3.1 |
| EGFR L858R | 6.3 | 2.7 |
| EGFR L858R/T790M | 924 | 77.7 |
| T790M | 1011 | 54.7 |

The kinase selectivity against a panel of 92 wild-type kinases, chosen to represent the diversity of the kinome, was determined for Compound (IIa) and gefitinib. The residual activity of the compounds was determined at 100 nM and 1 µM following the same protocol as IC$_{50}$ determination. Corresponding kinases and substrates were always tested at the ATP Km concentration. The selectivity is represented on a dendrogram with dot size proportional to residual activity. The selectivity score S(50) is calculated as followed:

$$S(50) = \frac{\text{(number kinases inhibited)} > 50\%}{\text{number of tested kinases}}$$

The selectivity was very good since EGFR and RIPK2 were the only wild-type kinases inhibited for more than 50% by Compound (IIa) at the concentration of 100 nM (data not shown). This profile is comparable to the one for gefitinib. At 1 µM, which corresponds to a fold>100 compared to primary activity against EGFR WT or EGFR_L858R mutant, we observed an inhibition of >50% on 9 other kinases (2 other kinases for gefitinib). The selectivity scores S(50) is 2.2% and 11.9% respectively at 100 nM and 1 µM.

The selectivity scores S(50) of compound (IIa)—Pure S—enantiomer is 2.5% and 13% respectively at 100 nM and 1 µM.

The selectivity scores S(50) of compound (IIIa)—Pure R—enantiomer is 0.6% and 2.8% respectively at 100 Nm and 1 µM.

Cellular Activity

The cell lines that were used to assay the cellular activity of the compounds are detailed in table 3 hereafter:

TABLE 3

Cell lines description and respective EGFR mutation status

| Cell line | Type | EGFR mutation status | Species |
|---|---|---|---|
| NCI-H441 | Lung papillary adenocarcinoma | WT | Human |
| NCI-H3255 | Lung adenocarcinoma | Simple mutation, L858R | |

TABLE 3-continued

Cell lines description and respective EGFR mutation status

| Cell line | Type | EGFR mutation status | Species |
|---|---|---|---|
| NCI-H1975 | Adenocarcinoma non-small cell lung cancer | Double mutation, L858R/T790M | |
| MCF-7 | Pleural effusion adenocarcinoma | Very low to none expression, WT | |

Tumor cells grew as monolayer at 37° C. in a humidified atmosphere (5% CO2) in complete culture medium adapted to each cell line. The cellular activity of the compounds was assessed by measuring the viability of cancer cell in MTS assay using a tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). MTS is bioreduced by cells into a formazan product that is directly soluble in culture medium without processing. The cells were seeded 24 hours before treatment at the appropriate density in their culture medium to be near 90% of confluence at the end of experiment in vehicle treated conditions. After addition of compounds, the cells were incubated for 72 hours.

As shown in table 4, the cellular activities are in the same range for Compound (IIa) and gefitinib. Compound (IIIa) showed a very high activity on NCI-H3255 (mean $IC_{50}$ of 6.1 nM) and a moderate activity on NCI-H1975 (mean $IC_{50}$ of 5 µM), whereas it has a weak activity on NCI-H441 (mean $IC_{50}$ of 34.7 µM). A set of experiments was also performed on MCF-7 which does not express EGFR (negative control). Compound (Ia) and the corresponding S (IIa) and R (IIIa) enantiomers have a very weak activity on MCF-7 ($IC_{50}$ of 62.1 µM) suggesting a good cellular selectivity.

TABLE 4

$IC_{50}$ of Compound (Ia), compound (IIa) (i.e. Pure S-enantiomer) and compound (IIIa) (i.e. Pure R-enantiomer) compared to gefitinib determined by MTS assay performed on NCI-H441, NCI-H3255, NCI-H1975 and MCF-7

| Cellular $IC_{50}$ (µM) | Compound (Ia) | Compound (IIa)- Pure (S)-enantiomer | Compound (IIIa)- Pure (R)-enantiomer | Gefitinib |
|---|---|---|---|---|
| NCI-H441 (EGFR WT) | 34.7 ± 24 | >25 | >25 | 14.9 ± 2.7 |
| NCI-H3255 (EGFR_L858R) | 0.006 ± 0.002 | 0.030/0.049 | 0.0008/0.056 | 0.012 ± 0.007 |
| NCI-H1975 (EGFR L858R/T790M) | 5.0 ± 1.4 | 10/25 | 20/25 | 17.7 ± 5.9 |
| MCF-7 | 62.1 | >25 | >25 | |

Effect of Compounds on EGFR Phosphorylation

To evaluate the inhibition of EGFR phosphorylation induced by Compound (Ia) compared to gefitinib, cells were treated with a dose range of each compound and induced with 10 ng/ml of EGF. Effect on $Y_{1068}$ phosphorylation was observed by Western blot (data not shown). On NCI-H441, Compound (Ia) inhibited the phosphorylation induced by EGF, at a slightly better level than gefitinib, with almost full inhibition observed at 1 µM. On NCI-H3255, the full inhibition of constitutively active EGFR was observed. This kinase inhibition was observed approximately at 100 nM for Compound (Ia), at a level similar to gefitinib inhibition. On the constitutively active double mutant EGFR expressed by NCI-H1975, the gefitinib is not active at the top dose of 1 µM, as this cell line acquired resistance to this drug through T790M mutation. Interestingly, Compound (Ia) seemed to partially inhibit EGFR activity at 10 µM while gefitinib did not, showing again the slightly better inhibition of EGFR kinase activity of this new fluorinated compound compared to gefitinib.

Solubility and Stability

The kinetic solubility of the compounds was assessed in PBS at pH 7.4. Compound (Ia) showed a good solubility of 88 µM in PBS (Table 5).

TABLE 5

Solubility and stability of Compound (Ia) and Compound (I)

| Parameter | | Result |
|---|---|---|
| Kinetic solubility at pH 7.4 (µM) (Compound Ia) | | 88 |
| Radiochemical stability (h) (Compound I) | | >20 |
| Plasmatic stability (h) (Compound Ia and I) | | >4 |
| human microsomal stability (Compound Ia) | Clint (µL/min/mg prot.) | 7.76 ± 2.53 |
| | t1/2 (min) | 179 |
| rat microsomal stability(Compound Ia) | Clint (µL/min/mg prot.) | 37.9 ± 1.89 |
| | t1/2 (min) | 36.5 |

After radiosynthesis, the stability of the radiotracer was evaluated by HPLC both in its vehicle and in rat plasma. Compound (I) was formulated in physiologic serum/ethanol with the respective proportion 87.5/12.5 (v/v). A mixture of compounds (I) (i.e. radiolabelled) and (Ia) (i.e. cold analogue) was stable for up to 20 hours at room temperature in its vehicle, only one peak being detected at the expected retention time. In rat plasma two peaks were detected: one at 3.15 minutes and one at 8.02 minutes (corresponding to a mixture of compounds (I) and (Ia)) after an incubation at +37° C. for 4 hours. The area of the peak corresponding to said mixture accounted for >95% of the total area of both peaks, indicating that said mixture was stable in human plasma for up to 4 hours (data not shown).

Metabolic microsomal stability was performed on human and rat liver microsomes. Microsomes (final protein concentration 0.5 mg/mL), 0.1 M phosphate buffer pH 7.4 and test compound (final substrate concentration=3 µM; final DMSO concentration=0.25%) are pre-incubated at 37° C. prior to the addition of NADPH (final concentration=1 mM) to initiate the reaction. Analysis is done with generic LC-MS/MS conditions to determine half-life and intrinsic clearance using standard equations. Microsomal stability study showed, in rat, a half-life in the range of 40 minutes for both fluorinated compounds and a clearance superior to 30 µL/min/mg of proteins (Table 5). In human, Compound (Ia) metabolic stability was better than in rat and favorable for clinical studies.

In Vitro Binding Evaluation of Compound (I) in Cellular or Tumor Samples

The binding affinity of Compound (I) and the number of binding sites were first evaluated on NCI-H3255 and NCI- H441 tumor cell homogenates (FIG. 1). The binding affinity (Kd) of Compound (I) on NCI-H3255 tumor cell homogenates was 23.8±9.0 nM and the number of binding sites was $9.1±3.1×10^9$ sites/μg protein. The affinity of Compound (I) on NCI-H441 tumor cell homogenates was 25.8±11.1 nM, being similar to that determined in NCI-H3255 tumor cell homogenates. The number of binding sites was of the same order of magnitude ($6.1±0.5×10^9$ sites/μg protein).

Figure 2:
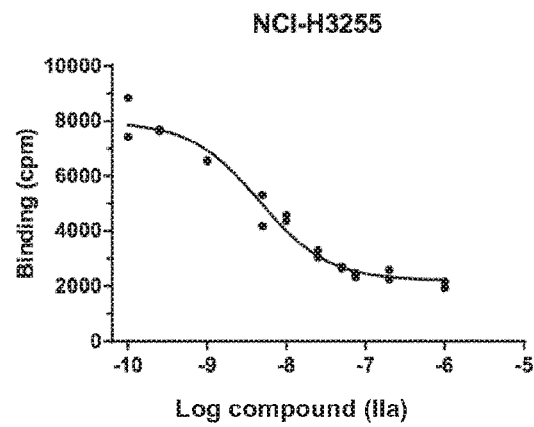
FIG. 2: Binding affinity constant of Compound (II) determined in competition experiments on NCI-H3255 (A) and NCI-H1975 (B) tumor extracts. NCI-H3255 and NCI-H1975 tumor extracts were incubated at room temperature for 90 min with Compound (II) (0.1-0.3 nM) and with increasing concentrations of Compound (IIa) (0.25 nM to 1 µM).
Figure 2:
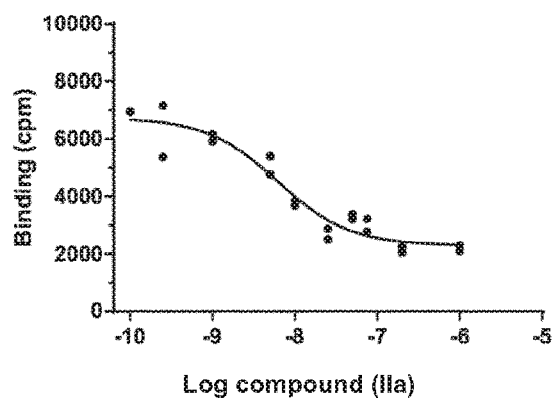

Similar experiments were performed on NCI-H3255 and NCI-H1975 tumor homogenates (FIG. 2). Binding affinities were similar: 2.8±2.4 nM and 4.7±2.0 nM for NCI-H3255 and NCI-H1975 tumor homogenates, respectively. The number of binding sites was $1.1±1.5×10^9$ and $1.6±1.8×10^9$ sites/μg protein respectively in NCI-H3255 and NCI-H1975 tumor homogenates.

Considering the NCI-H3255 cell line extract and tumor homogenate, affinity and number of binding sites obtained for cell and tumor homogenates appeared consistent: binding affinity of the same order of magnitude and number of binding sites 8-fold lower in tumor homogenates than in tumor cell homogenates. The lower number of binding sites reflects most likely the lower number of tumor cells in tumor homogenates due to the presence of stroma cells.

Figure 3:
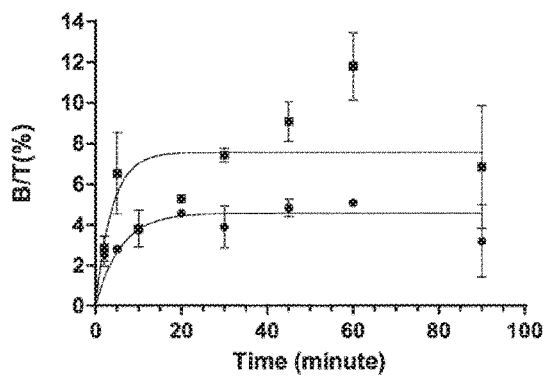
FIG. 3: Binding kinetic of Compound (II) evaluated on NCI-H3255 (A) and NCI-H1975 (B) tumor extracts. Compound (II) (1.5-2.5 nM) was incubated with extracts for 2 to 90 minutes at room temperature. Non-specific binding was evaluated in the presence of a>100 fold excess Compound (IIa).
Figure 3:
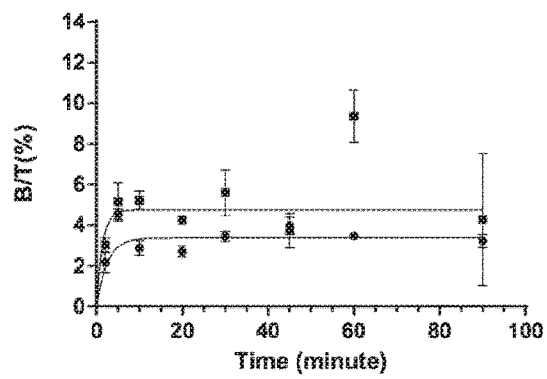

The binding kinetic of Compound (I) was also assessed in NCI-H3255 and NCI-H1975 tumor homogenates (FIG. 3). The dissociation constant ($K_{off}$) of Compound (I) was slightly lower in NCI-H3255 homogenates than in NCI-H1975 tumor homogenates (0.114±0.001 vs 0.270±0.109 $min^{-1}$, respectively) while the association constant ($K_{on}$) was slightly higher in NCI-H1975 tumor homogenates than in NCI-H3255 tumor homogenates ($6.5±5.3×10^7$ $L·mol^{-1}·min^{-1}$ vs $1.8±1.6×10^7$ $L·mol^{-1}·min^{-1}$, respectively). Binding kinetic data show that Compound (I) binds to its target and is released faster in NCI-H1975 than in NCH-H3255 tumor homogenates.

As in vitro data showed that Compound (I) specifically bound to activated EGFR, autoradiography experiments on human frozen tumor sections were initiated (data not shown). Three types of human lung tumors were included: tumors harboring wild type EGFR and tumors carrying L858R mutated or exon 19 deleted EGFR genes. Binding competition with gefitinib and ATP was also evaluated on these frozen tumor sections. A specific binding of Compound (I) was observed on all tumor types. Gefitinib competed with the binding of Compound (I) but only partially while ATP (at 10 mM) totally abolished the binding of Compound (I) (data not shown). Data suggest that the displacement observed in the presence of Gefitinib may be higher on tumors harboring the L858R mutation or the deletion of exon 19 as compared to wild type tumors.

In vitro experiments showed that a mixture of compounds (I) and (Ia) specifically bound to its target, that is presumably activated EGFR. The binding affinity of said mixture was in the nanomolar range which is suitable for in vivo studies.

PET Imaging and In Vivo Biodistribution Studies of Compound (I) in Tumor-bearing Rats Dynamic PET scan imaging and ex vivo gamma counting were performed on three cancer xenografts (NCI-H441, NCI-H3255, NCI-H1975) in Nude rats. Xenografts were initiated in athymic, Hsd:RH-Foxnlrnu rats (Harlan, The Netherlands) by subcutaneous injection of $2×10^7$ cells in 200 μL RPMI 1640 in the left and right flanks. NCI-H3255 tumor cells were injected in the right flank and NCI-H441 or NCI-H1975 in the left flank. Each study consisted in two experiments on 18 or 19 rats, for a total of 113 rats. Injection of NCI-H3255 cells was performed on D0, 24 to 72 hours after a whole-body irradiation with a ©-source (5 Gy, $^{60}Co$, BioMep SARL, Bretenières, France). Injection of either NCI-H441 or NCI-H1975 cells was performed 20 to 29 days post injection of NCI-H3255 cells to ensure a comparable volume for both tumors at the time of experiment. Tumors were grown until a target volume of 500-1500 $mm^3$ for both tumors was reached, whenever possible. All procedures using animals were approved by the Animal Care and Use Committee of Oncodesign (CNREEA agreement No 91).

The radiotracer solution was diluted in NaCl 0.9% to prepare a solution of activity 4-6 MBq (gamma-counting experiments) or 25-35 MBq (PET imaging experiments) in a volume of 300-400 or 600-800 μL, respectively. The radioactivity in the syringe was measured before and after tracer injection to determine the injected dose (ID) to animals. Rats were anesthetized with inhaled isoflurane (2% in air) for compound injection and throughout the course of image acquisition. After compound injection, rats were allowed to wake up and put back in their cage for an uptake period ranging from 20 to 120 minutes depending on the experiment.

For ex vivo gamma counting, after the determined uptake period or after imaging, rats were euthanized by decapitation, and the following organs were harvested and weighed: tumor, kidneys, blood, liver, heart, tail, thigh muscle, lungs, spleen and skin. Tracer distribution was assessed by determining $^{18}F$ content in each tissue with a gamma-well counter (PerkinElmer 2480 Wizard2 3). Counting data are reported as % ID per gram of tissue (% ID/g). Once radioactivity in organs was measured, some samples were prepared for immunohistochemistry.

For imaging experiments, rats were positioned prone in a dedicated rat imaging chamber (Minerve, France). Their body temperature was maintained by a flow of warm air through the structure of the imaging bed. PET imaging was performed on a microPET eXplore Vista CT (General Electric Healthcare) system. The Vista system, equipped with 36 dual-layer LYSO/GSO phoswich detector modules, has an effective axial/transaxial field of view of 4.8/6.7 cm. The spatial resolution is <2 mm in all directions and in the whole field of view. The sensitivity is above 2.5% in the whole field of view. After a scout image to adjust the position of the field of view, a CT scan was acquired (140 μA, 40 kV). One minute after initiation of PET image acquisition, Compound (I) was administered into a lateral tail vein via an i.v. line and flushed with a saline solution. Three-dimensional (3D) PET data were acquired in list mode for up to 120 minutes and reconstructed using OSEM-2D to create two data sets: one static image as the sum of data during the whole acquisition, and a set of dynamic images with time frames of 10 minutes. Corrections for attenuation, scatter, dead time, detector sensitivity, and randoms were applied to emission data. Both data sets had a spatial resolution of 0.4×0.4×0.8 mm and a size of 175×175×61 voxels. All rats were euthanized immediately after PET data acquisition by decapitation, and organs were harvested as described in the previous paragraph to obtain biodistribution data corresponding to PET image data.

The reconstructed PET/CT images were viewed and analyzed in dedicated software (PMOD, version 3.4). Regions of interest (ROI) were manually drawn in CT images and, after manual registration of PET and CT images, decay-corrected activity data were obtained (in $kBq/cm^3$, normalized by ROI volume). Compound (I) time-activity curves (TAC) were generated for each ROI by averaging over frames of 10 minutes. For the purpose of display, we also generated images from the static scan summed over the whole tumor volume (6 to 10 slices in the PET volumetric data set).

In Vivo Biodistribution Studies of Compound (I)

Figure 4:
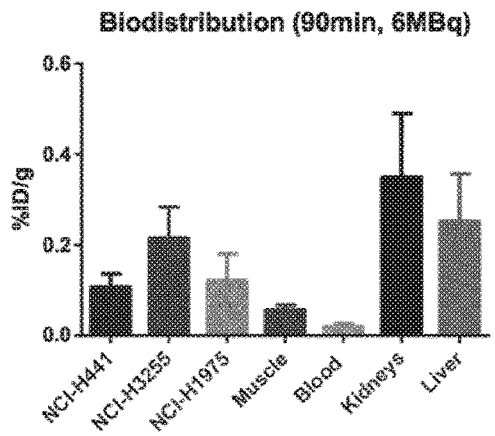
FIG. 4: Biodistribution of Compound (II) in several cell lines and the main organs (in % ID/g) 90 min, 6MBq (A); or 180 min, 30 MBq (B); and uptake in blood (C), muscle (D) and tumors (E).
Figure 4:
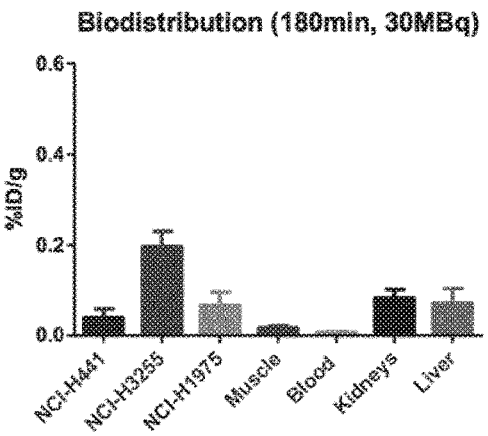
Figure 4:
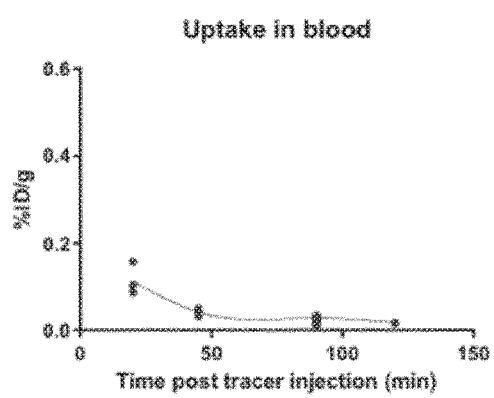
Figure 4:
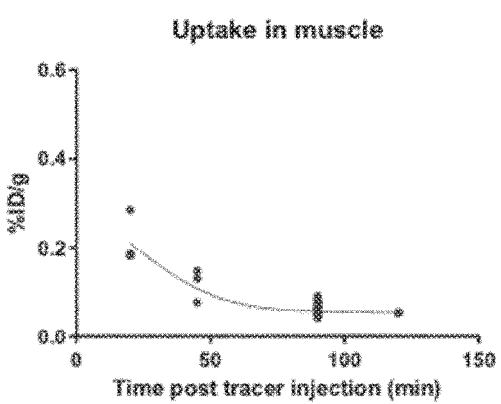
Figure 4:
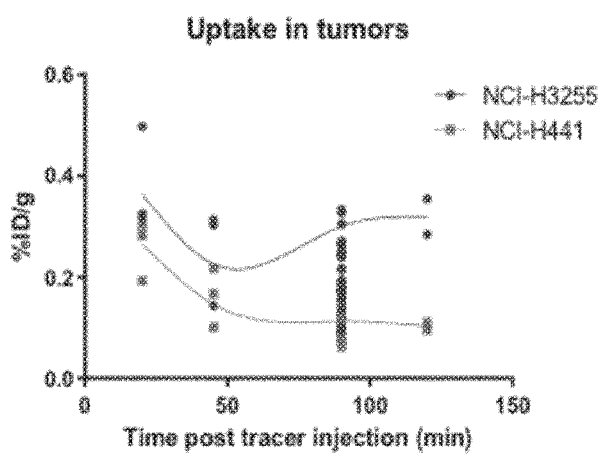
Figure 5:
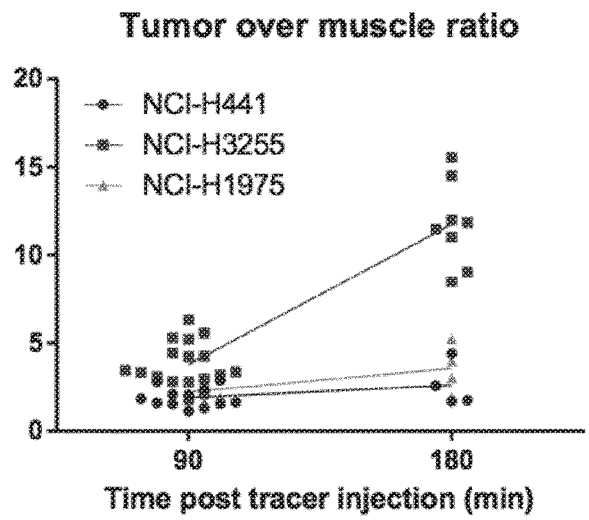
FIG. 5: Normalized uptake of Compound (II)—ratio of tumor over muscle

Compound (I) was rapidly cleared from the blood (<0.05% ID/g after 45 min, FIG. 4). Compound (I) showed initial uptake in the kidneys and liver, but did not accumulate in these organs. Compound (I) also showed central accumulation and excretion through the gastrointestinal tract. Uptake of Compound (I) was higher in NCI-H3255 tumors than in NCI-H441 or NCI-H1975 tumors, both 90 minutes and 180 minutes post injection. Uptake decreased between 90 min and 180 min in all organs and tumors, except in NCI-H3255, where it stayed stable (around 0.2% ID/g). The absolute uptake in tumors was relatively low, (<0.5% ID/g at 90 min, see FIG. 4), but the normalized uptake (over muscle) increased between 90 min and 180 min in NCI-H3255 to reach a value of 12 at 180 min (NCI-H441: 2.6; NCI-H1975: 3.6, see FIG. 5).

PET Imaging of Compound (I) in Tumor-bearing Rats

For all three tumor models, representative PET images show the difference in uptake measured by in vivo imaging in tumors between the WT, the single-mutation and the double-mutation models (data not shown). Uptake is confirmed by the distribution of harvested activity strongly correlated with distribution observed in PET images (FIG. 6).

Figure 6:
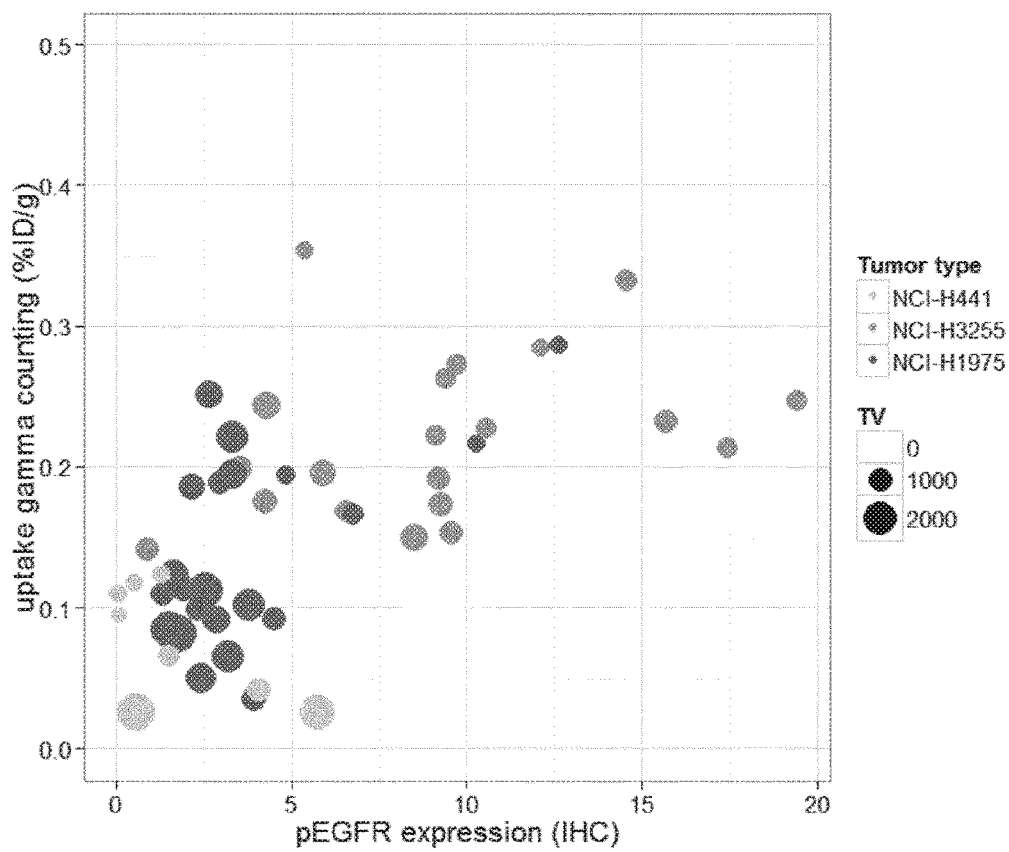
FIG. 6: Uptake in tumors measured by harvesting tumors and counting radioactivity in relation with PET imaging

As shown in FIG. 6, uptake measures by PET imaging or by counting radioactivity in collected tumors were strongly correlated. Our experiments can then be described by studying relationships between tumor models (EGFR mutation status), radiotracer uptake measured on harvested tumors (in % ID/g), pEGFR staining measured by immunohistochemistry (IHC) on these tumors, and tumor volume. For IHC, xenografts were dissected and fixed in formalin-buffered saline for 24 hours followed by 70% ethanol before paraffin embedding and sectioning (thickness: 4 µm). EGFR phosphorylation was determined by immunostaining with an antibody against pEGFR (phospho Y1068, Abcam, ref ab32430) using an automated staining instrument (Ventana Discovery, Roche) and necrosis was evaluated on hematoxylin and eosin (H&E) stains. Negative controls were prepared omitting the primary antibody and showed no staining. Slides were digitized using a Nanozoomer slide scanner (Hamamatsu, ×20 magnification) for image analysis and quantification.

Necrosis was evaluated by manual delineation of necrotic zones in tumors using NDPView (Hamamatsu, France) and reported as a percentage of necrotic surface area over the whole tumor tissue area. Staining of pEGFR was quantified using NDPView and Visilog (FEI Visualization Sciences Group, France) by thresholding and manual delineation of viable tumor tissue and tissue positive for pEGFR. Intensity of pEGFR is reported as the product of the number of pEGFR+ pixels and their average staining intensity, over the area of viable tumor tissue in $\mu m^2$.

Figure 7:
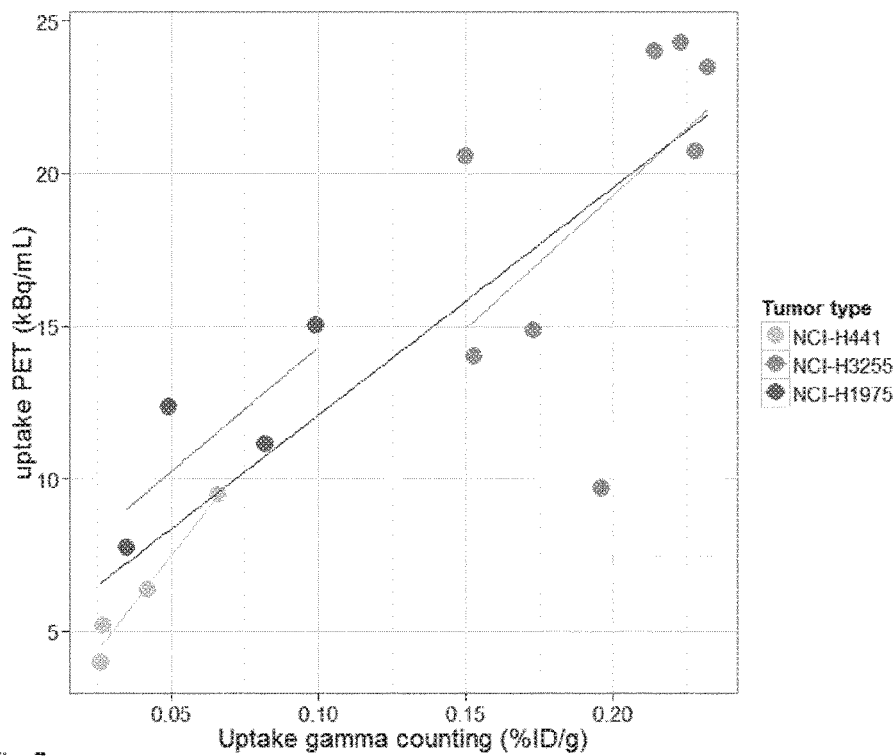
FIG. 7: Relationship between uptake measured from collected tumors and pEGFR intensity measured by immunohistochemistry (IHC), taking into account tumor volume as a confounding factor (A): pEGFR versus uptake, with tumor volume shown as the area of the point, for all three tumor models. B-D: for each model NCI-H441 (B), NCI-H3255 (C) and NCI-H1975 (D), correlation of uptake and pEGFR determined for tumor volumes below 1000 mm$^3$ (black dots) or over 1000 mm$^3$ (gray triangles).
Figure 7:
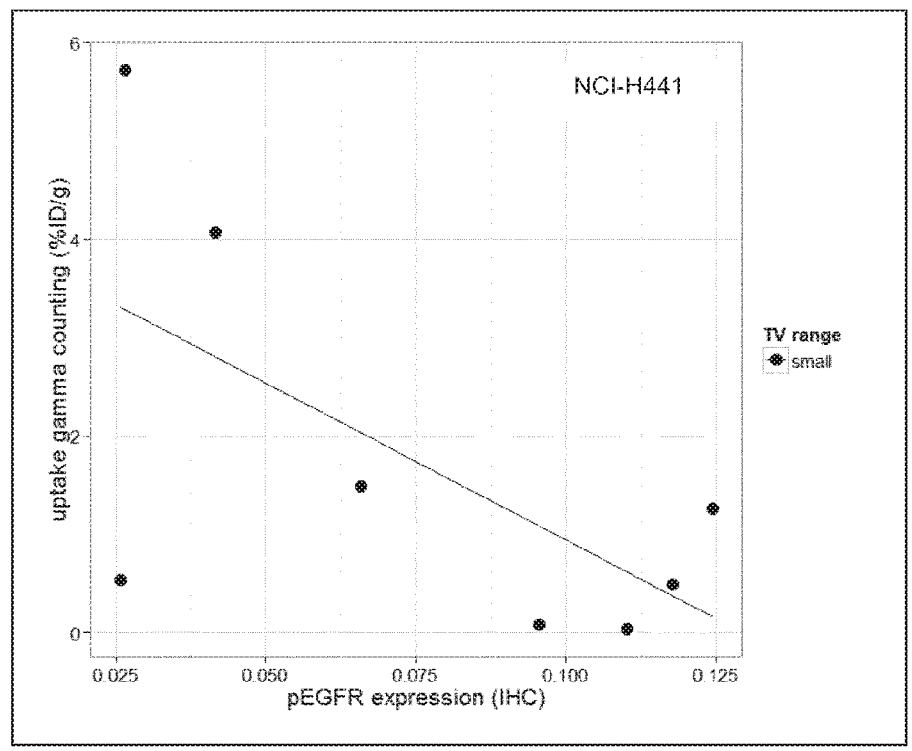
Figure 7:
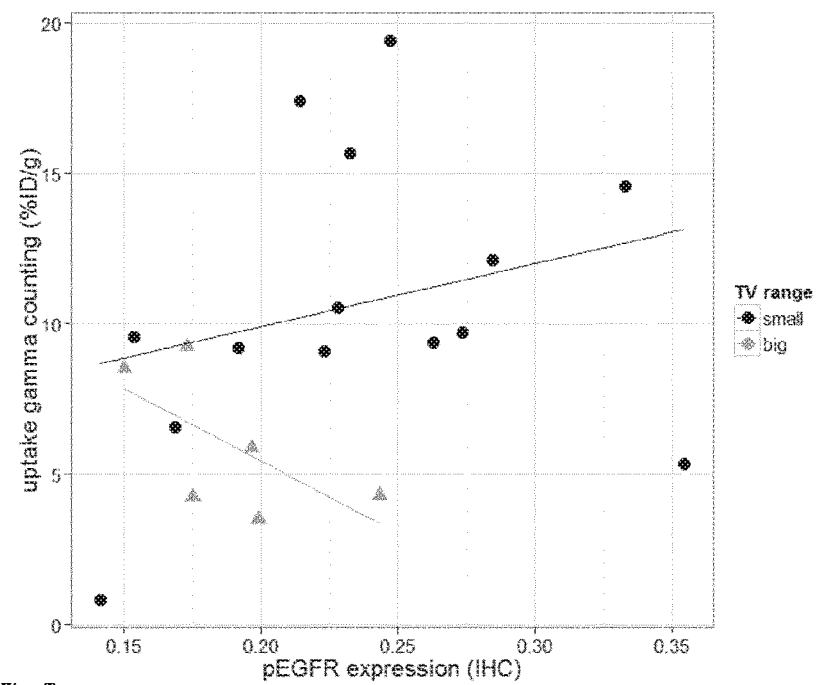
Figure 7:
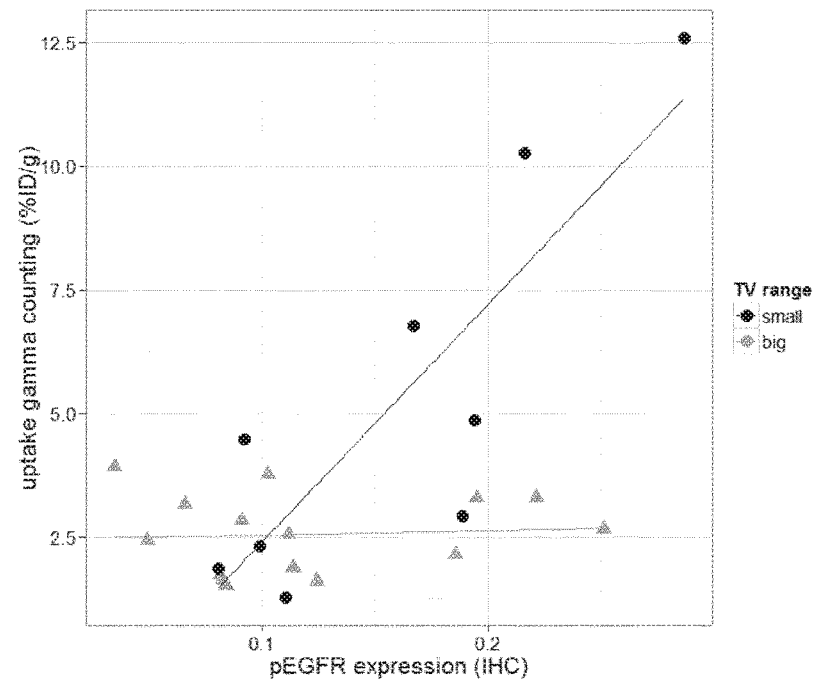

FIG. 7 (top row) shows that double-mutation tumors were comparably bigger than the other two models, and that pEGFR intensity was lower in bigger tumors. We therefore divided the measurements into subsets based on tumor volumes (below and above 1000 $mm^3$). In terms of tumor biology, this threshold represents the volume at which necrosis starts to appear. FIG. 7 also shows that this partition allows to identify a correlation between EGFR activity and measured radiotracer uptake in both single- and double-mutation models, in smaller tumors, while this correlation disappears in bigger tumors. For the WT tumor model, this correlation is not observed regardless of tumor volume.

In Vivo Specificity of Compound (I)

Figure 8:
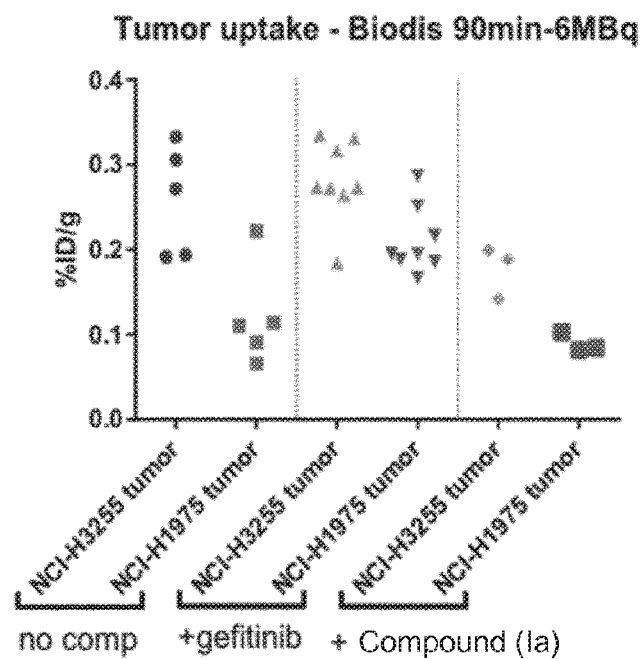
FIG. 8: Normalized tumor uptake with or without competition with either gefitinib or Compound (IIa). (in % ID/g). (A) Tumor uptake—Biodis 90 min, 6MBq; (B) Tumor uptake—Biodis 180 min, 30 MBq; (C) T/M—Biodis 90 min, 6MBq; (D) T/M—Biodis 180 min, 30 MBq
Figure 8:
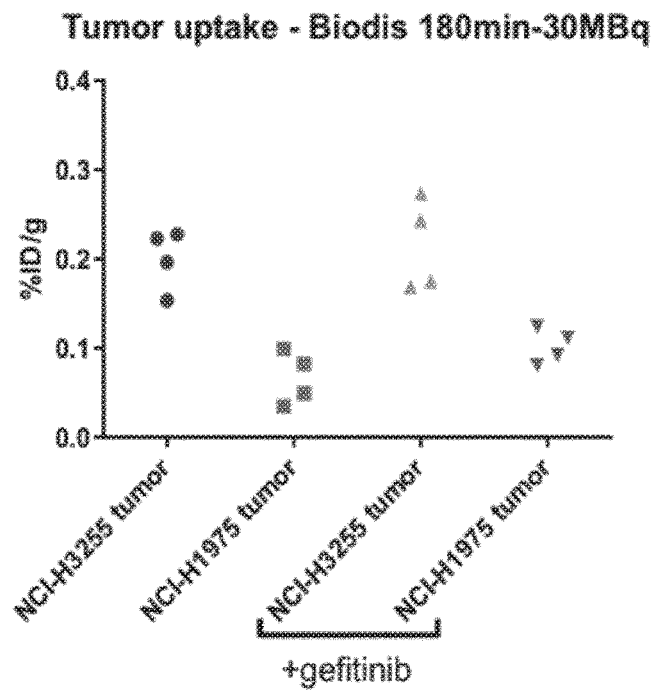
Figure 8:
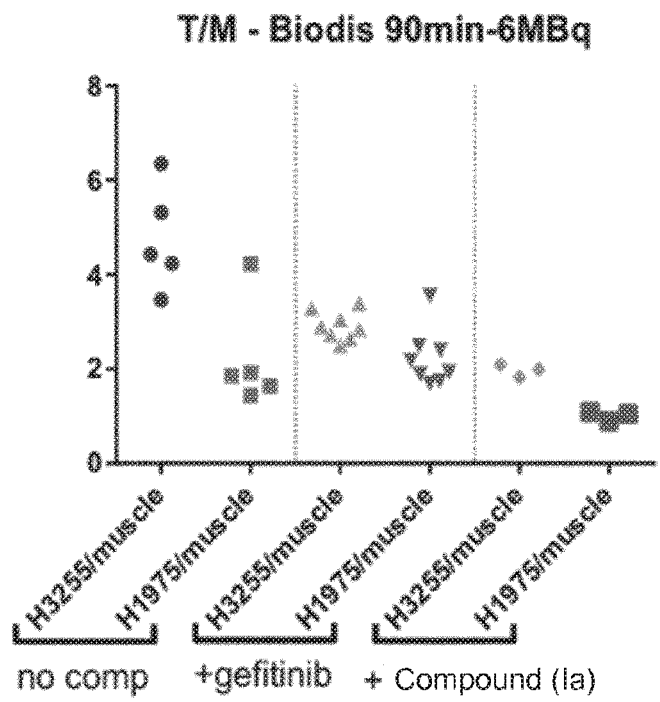
Figure 8:
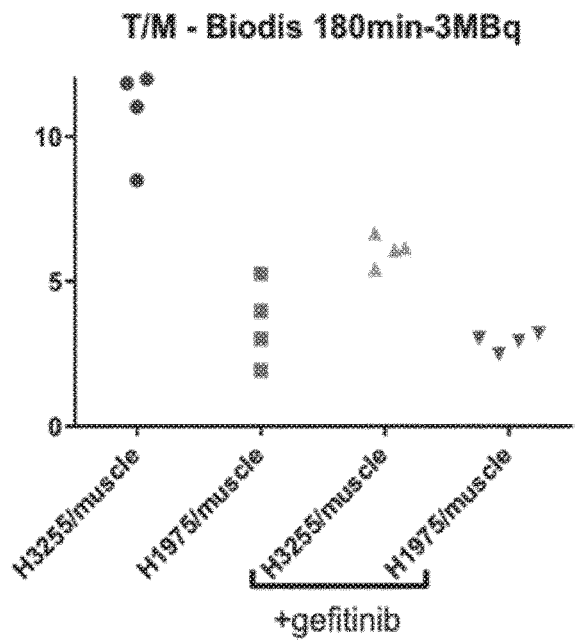

To evaluate the selectivity of Compound (I) for imaging activated EGFR in the three tumor models, rats were injected with either gefitinib (2 mg/rat, for an approximate dose of 10 mg/kg) or the non-radioactive (or cold) tracer Compound (Ia) (1 mg/rat, approximate dose: 5 mg/kg) in large excess to compete for its target. Normalized uptakes and ratios of tumor over muscle uptakes are presented in FIG. 8.

Competition with neither gefitinib (+16%, p>0.95) nor Compound (Ia) (5%, p>0.99) modified the uptake of Compound (I) in WT NCI-H441 tumors. For NCI-H3255 tumors (simple mutation), T/M ratios are decreased by 29% by gefitinib competition (p<0.01) and by 52% (p<0.001) by Compound (Ia) competition. This shows the specificity of the radiotracer for EGFR as a common target in this tumor model. For NCI-H1975 tumors (double mutation), gefitinib does not have any influence on T/M ratios (+1%, p>0.99), but we have observed a marked but statistically non-significant decrease (−55%, p=0.2) after competition with Compound (Ia).

Overall, this PK profile is favorable for the use of Compound (I) as a radiotracer, provided a sufficiently long uptake period is observed before imaging.

Overall, Compound (I) is a good PET radiotracer candidate to evaluate by PET imaging in human lung tumors the EGFR activity in correlation with its mutational status.

In Vivo Biodistribution of Compound (I) and Pure S (II) or R (III) Enantiomers

To evaluate the biodistribution of the pure S (II) and R (III) enantiomers compared to compound (I), dynamic PET scan imaging and ex vivo gamma counting were performed on Sprague Dawley rats. Animals were injected with the radiotracer solution diluted in NaCl 0.9% to prepare a solution of activity 4-6 MBq (gamma-counting experiments) or 11-13 MBq (PET imaging experiments) in a volume of 300-400 or 600-800 µL, respectively. Radioactivity content in all biological samples was determined with scintillation γ-counter (Cobra 4180, Perkin-Elmer Inc.).

At the light of the biodistribution data of compound (I), the biodistribution of the R (III)- and S (II)-enantiomers was assessed by γ-counting in the organs in which the accumulation of compound (I) was prominent (that is: blood, heart, kidneys, liver, stomach, small intestine and colon). Two timepoints were selected: 5 and 30 minutes post-injection. The choice of these two timepoints was driven by the fact that compound (I) did not accumulate in blood, liver and kidneys. The higher uptakes of R enantiomer (III) and S enantiomer (II) in these organs were expected to be observed at early timepoints after injection, giving the highest signals in the γ-counter and therefore making the comparison of biodistribution data more relevant. Besides, as PET images were acquired with compound (I), PET imaging was included in the evaluation of the biodistribution of R enantiomer and S enantiomer. This gave the opportunity to had one additional timepoint at 4 hours post-injection for collection of major organs and determination of radioactivity content by ex vivo γ-counting.

On the 5 minutes, post-injection timepoint, uptake in blood reached 0.20±0.002% ID/g for R enantiomer (III) and 0.11±0.01% ID/g for S enantiomer (II) (while the uptake was 0.13±0.02% ID/g for compound (I). On the 0.5 hour timepoint, radioactivity uptake was similar for the three tracers (close to 0.03-0.04% ID/g). Similarly, uptake at 4 hours post-injection was in the same range of magnitude for the three tracers (0.02-0.04% ID/g). The behavior of R enantiomer (III) and S enantiomer (II) in blood was similar to that of compound (I).

Five minutes after the injection, the uptake in heart of R enantiomer (III) and S enantiomer (II) reached 0.99±0.02 and 1.35±0.35% ID/g, respectively, these uptakes being comparable to that of compound (I) (0.91±0.12% ID/g). At 30 minutes post-injection, uptakes were similar for R enantiomer and S enantiomer (0.10±0.02 and 0.19±0.08% ID/g) and were still comparable to that of compound (I) (0.23±0.05% ID/g). On the 4 hours timepoint, uptake of the three tracers had decreased to 0.01% ID/g.

Five minutes post-injection, the uptake of R (III) and S (II) enantiomer in kidneys were similar to that of compound (I): 4.15±0.79 and 6.89±0.52% ID/g vs 5.07±0.30% ID/g, respectively. On the 30 minutes timepoint, uptake in kidneys was of the same order of magnitude for S enantiomer (II) and compound (I) (1.04±0.17 and 1.47±0.36% ID/g, respectively) but was lower for R enantiomer (III) (0.25±0.08% ID/g). For this last tracer, individual uptakes recorded 30 minutes post-injection were lower than the lowest individual value recorded for compound (I) at the same timepoint. Kidneys uptake was in the 0.01-0.05% ID/g for the three tracers 4 hours post-injection.

For R enantiomer (III), uptake in liver increased from 5 minutes to 30 minutes post injection: 0.02±0.09 to 0.71±0.07% ID/g, respectively. For S enantiomer (II), a decrease was noticed between 5 and 30 minutes post-injection: 0.97±0.92 to 0.15±0.03% ID/g as observed for compound (I) (1.66±0.43 to 0.37±0.07% ID/g). On the four hour timepoint, liver uptake did not exceed 0.02% ID/g for the three tracers.

The uptake in stomach of R enantiomer (III) and S enantiomer (II) was 1.86±0.73% ID/g and 0.72±0.38% ID/g, respectively, at 5 minutes post-injection. At this timepoint the uptake of compound (I) was 1.27±2.13%. The uptake of R enantiomer (III) and S enantiomer (II) declined to 0.26±0.07 and 0.20±0.05% ID/g on the 30 minutes timepoint, while a slight increase was noticed for compound (I) (2.72±4.75% ID/g). Four hours post-injection, uptake in stomach increased for R enantiomer (III) and S enantiomer (II) (2.58±2.52 and 2.39±2.31% ID/g) while it decreased for compound (I) (0.14±0.23% ID/g).

Uptake in small intestine reached 0.35±0.19 and 0.08±0.09% ID/g at 5 minutes post injection for R enantiomer (III) and S enantiomer (II), respectively, whereas the uptake was 0.28±0.15% ID/g for compound (I). Thirty minutes post-injection, uptake of R enantiomer (III) and S enantiomer (II) was lower than that of compound (I) (0.02±0.004 and 0.08±0.07% ID/g vs 0.40±0.40% ID/g, respectively). At 4 hours post-injection the uptake of R enantiomer (III) and S enantiomer (II) was similar to that of compound (I) (in the 0.6-0.8% ID/g range).

Uptake in colon of R enantiomer (III), S enantiomer (II) and compound (I) was in the 0.2-0.4% ID/g for the three tracers 5 and 30 minutes post-injection. Four hours post-injection the uptake of R enantiomer (III) and S enantiomer (II) remained close to 0.2-0.4% ID/g while uptake increased up to 10.55±4.53% ID/g for compound (I).

In summary, R enantiomer (III) and S enantiomer (II) were rapidly cleared from the blood as observed for compound (I). These two tracers were also eliminated from the body both via the kidney and the liver and were not trapped in these organs. As for compound (I), an uptake was noticed in stomach, small intestine and colon for R enantiomer and S enantiomer.

The overall behavior of R enantiomer (III) and S enantiomer (II) after an IV injection is comparable to that of compound (I). Pharmacokinetic profiles are similar for the three tracers.

Figure 9:
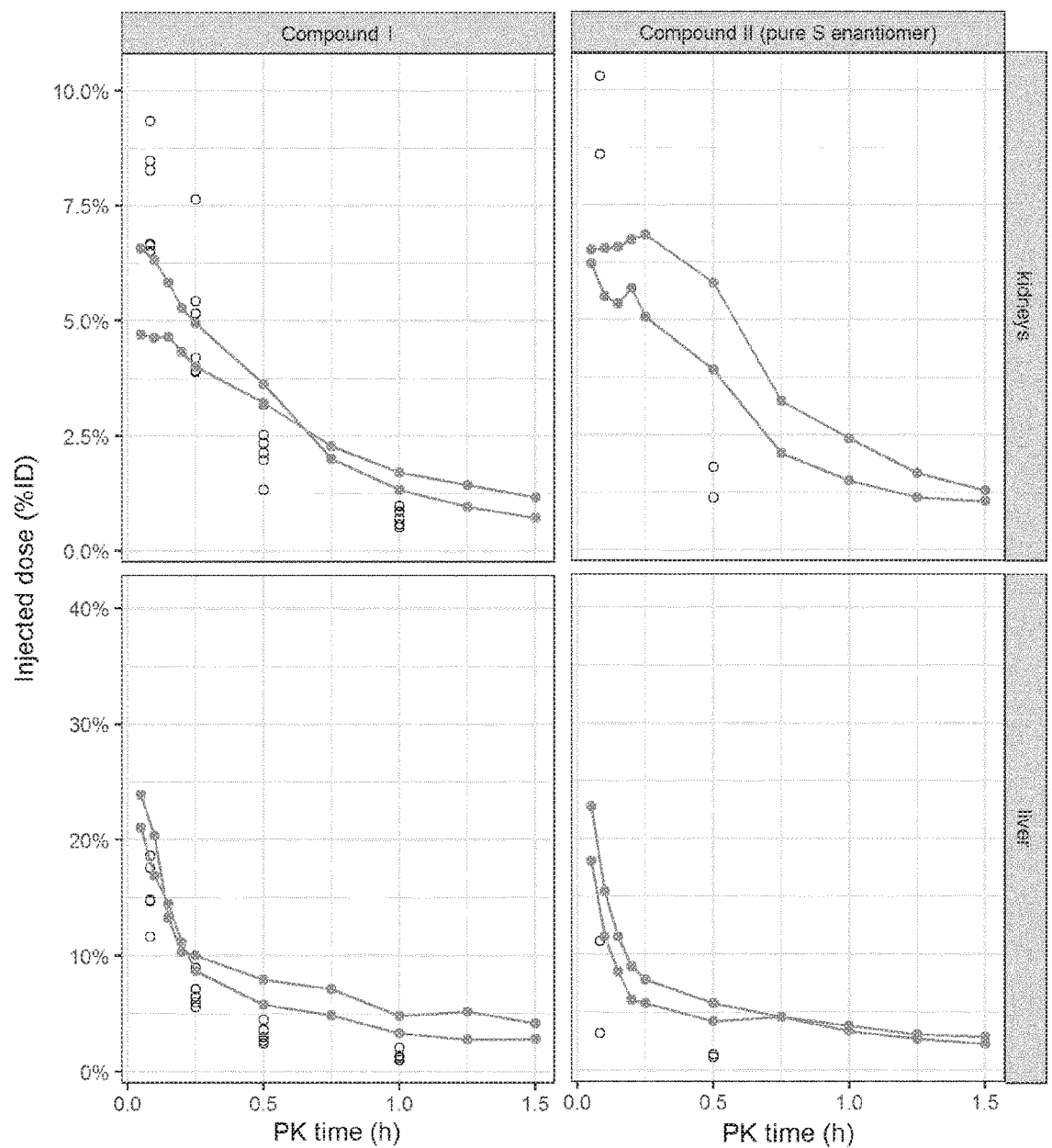
FIG. 9: Time activity curves (% injected dose corrected for radioactive decay as a function of time) of compounds I, II and III in mains organs measured by dynamic TEP after a single injection in Sprague-Dawley rats. (A) Results for compounds I, II and III in kidneys and liver; (B) Results for compounds I, II and III in intestines, kidney, liver and stomach.
Figure 9:
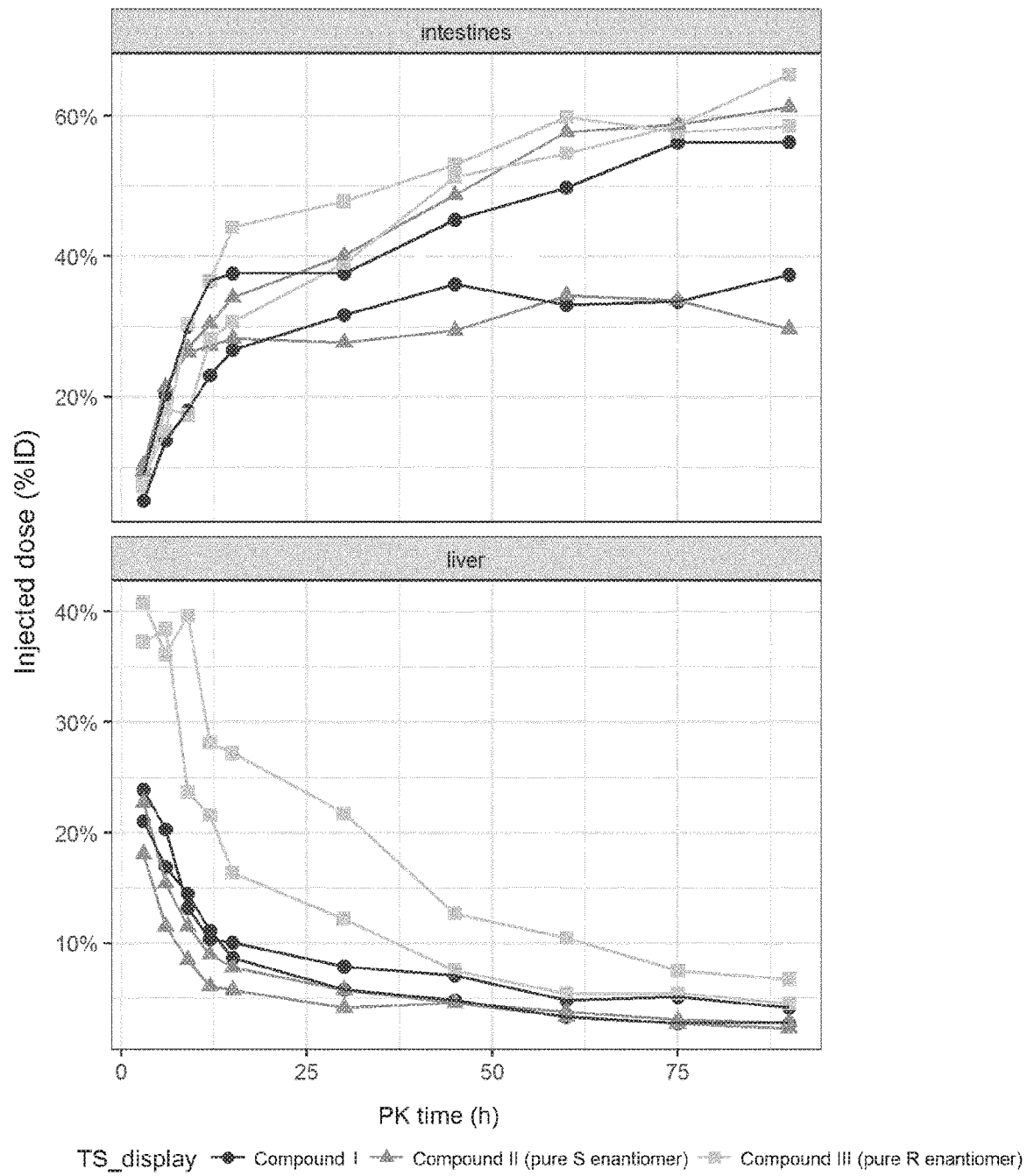

Uptake (% ID, corrected for radioactive decay) of compound (I), R enantiomer (III) and S enantiomer (II) in kidneys and liver determined by PET image analysis and ex vivo γ-counting are presented in FIG. 9(A). 90 minutes time-activity curves (% ID corrected for radioactive decay as a function of time) of compound (I), R enantiomer (III) and S enantiomer (II) in kidneys, intestine, stomach, and liver after a single IV injection in Sprague-Dawley rats are presented in FIG. 9(B).

The invention claimed is:

1. A fluorine-18 labeled compound of formula (I), or any pharmaceutically acceptable salt, polymorph, solvate, hydrate, stereoisomer, radioisotope or tautomer thereof

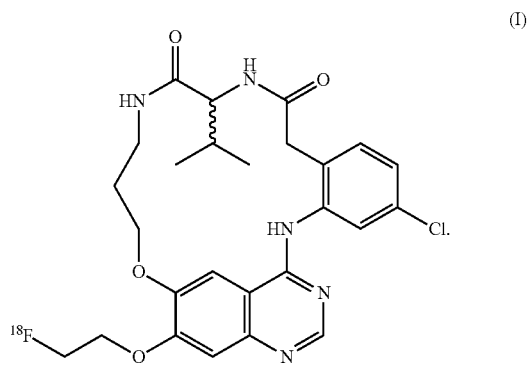 [SMILES: CC(C)C1NC(=O)Cc2ccc(Cl)cc2Nc2ncnc3cc(OCC[18F])c(cc23)OCCCNC1=O]

(I)

2. The fluorine-18 labeled compound claim 1, wherein the compound comprises the R-stereoisochemistry as represented in formula (III), or any pharmaceutically acceptable salt, polymorph, solvate, hydrate, stereoisomer, radioisotope or tautomer thereof

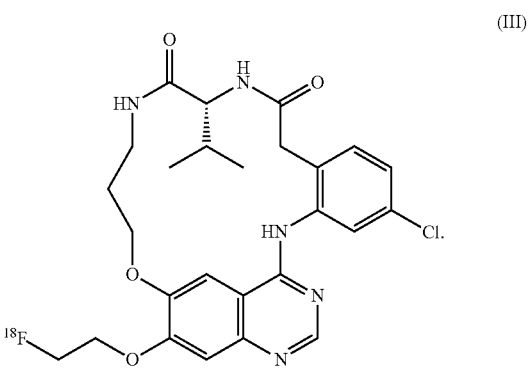 [SMILES: CC(C)[C@H]1NC(=O)Cc2ccc(Cl)cc2Nc2ncnc3cc(OCC[18F])c(cc23)OCCCNC1=O]

(III)

3. The fluorine-18 labeled compound claim 1, wherein the compound comprises the S-stereoisochemistry as represented in formula (II), or any pharmaceutically acceptable salt, polymorph, solvate, hydrate, stereoisomer, radioisotope or tautomer thereof (II)

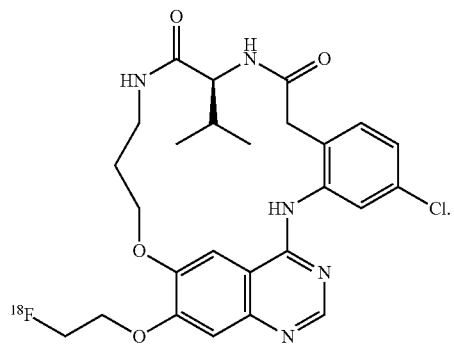

4. A radiopharmaceutical composition comprising:
a compound according to claim 1; and
at least one pharmaceutically acceptable carrier or diluent.

5. A method for imaging of an EGFR-associated tumor in a human, wherein the method comprises:
administering to a human an effective amount of a compound according to claim 1; and
obtaining an image useful for quantifying EGFR in the tumor of said human using positron emission tomography.

6. A method for the quantification of EGFR in human tissue, wherein the method comprises:
contacting such human tissue in which quantification is desired with an effective amount of a compound according to claim 1; and
detecting or quantifying EGFR using positron emission tomography.

7. A method for preparing a radiolabeled compound; said method comprising the steps of:
reacting radiolabeled

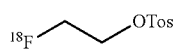

with a compound of formula (Ib)

(Ib)

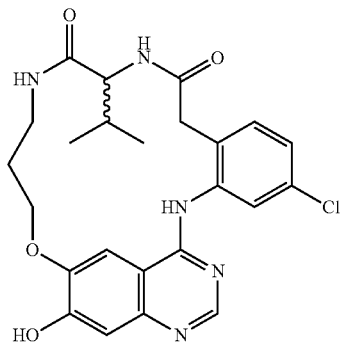

and isolating the resulting compound of formula (I)

(I)

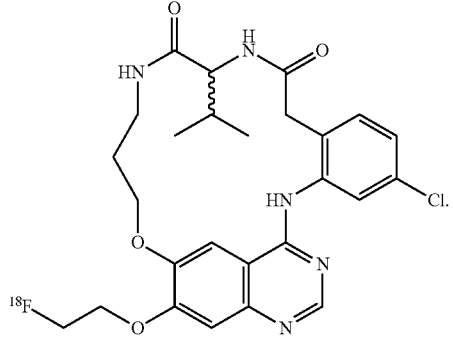

8. The method for preparing a radiolabeled compound according to claim 7;
wherein the compound of formula (Ib) comprises the R-stereoisomer as represented in formula (IIIb)

(IIIb)

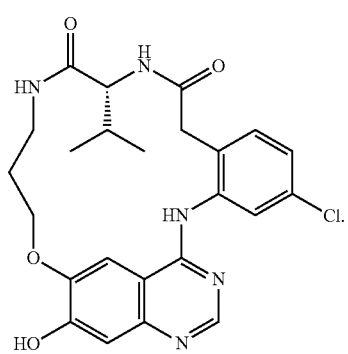

9. The method for preparing a radiolabeled compound according to claim 7;
wherein the compound of formula (Ib) comprises the S-stereoisomer as represented in formula (IIb)

(IIb)

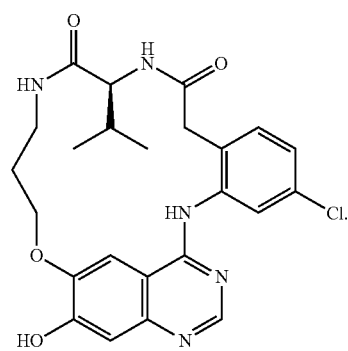

* * * * *

UNITED STATES PATENT AND TRADEMARK OFFICE
CERTIFICATE OF CORRECTION

PATENT NO. : 10,716,869 B2
APPLICATION NO. : 16/080196
DATED : July 21, 2020
INVENTOR(S) : Jan Marie Cyriel Jozef Hoflack et al.

It is certified that error appears in the above-identified patent and that said Letters Patent is hereby corrected as shown below:

On the Title Page

Item (72), inventor 7, name, delete "Gilles Voit" and insert --Gilles Viot--, therefor.

Column 2, item (56), other publications, cite no. 6, Line 23 delete "getitinib" and insert --gefitinib--, therefor.

Signed and Sealed this
Twentieth Day of October, 2020

Andrei Iancu
*Director of the United States Patent and Trademark Office*